(12) United States Patent
Kodama et al.

(10) Patent No.: US 11,862,321 B2
(45) Date of Patent: Jan. 2, 2024

(54) INGREDIENT DETERMINING DEVICE, INGREDIENT DETERMINING METHOD AND NON-TRANSITORY COMPUTER-READABLE RECORDING MEDIUM

(71) Applicant: TANITA CORPORATION, Tokyo (JP)

(72) Inventors: Miyuki Kodama, Tokyo (JP); Akiko Kubo, Tokyo (JP); Haruna Nakatani, Tokyo (JP); Masaki Yasuda, Tokyo (JP); Senri Tanida, Tokyo (JP); Toru Ichihashi, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 0 days.

(21) Appl. No.: 17/042,797

(22) PCT Filed: Mar. 12, 2019

(86) PCT No.: PCT/JP2019/010063
§ 371 (c)(1),
(2) Date: Sep. 28, 2020

(87) PCT Pub. No.: WO2019/188259
PCT Pub. Date: Oct. 3, 2019

(65) Prior Publication Data
US 2021/0027880 A1    Jan. 28, 2021

(30) Foreign Application Priority Data
Mar. 29, 2018 (JP) .................... 2018-066021

(51) Int. Cl.
*G16H 20/60* (2018.01)
*G16H 50/30* (2018.01)
(Continued)

(52) U.S. Cl.
CPC .............. *G16H 20/60* (2018.01); *A23L 33/30* (2016.08); *A61B 5/4519* (2013.01);
(Continued)

(58) Field of Classification Search
CPC ........ G16H 20/60; G16H 70/60; G16H 50/30; G16H 50/70; A23L 33/30; A61B 5/4519;
(Continued)

(56) References Cited

U.S. PATENT DOCUMENTS 5,415,176 A * 5/1995 Sato ..................... A61B 5/1075
600/587
6,327,494 B1 * 12/2001 Sakai ................... A61B 5/4872
600/547

(Continued)

FOREIGN PATENT DOCUMENTS

JP    2004-180939 A    7/2004
JP    2004-272618 A    9/2004
(Continued)

OTHER PUBLICATIONS

Lambert, Macronutrient considerations for the sport of bodybuilding, 2004, Sports Med, 34(5):317-27 (Year: 2004).*

(Continued)

*Primary Examiner* — Joshua B Blanchette
*Assistant Examiner* — Tran N Nguyen
(74) *Attorney, Agent, or Firm* — Studebaker & Brackett PC

(57) ABSTRACT

An ingredient determining apparatus configured to determine nutritional ingredients in food provided for a user. The ingredient determining apparatus includes a processor configured to obtain a muscle index indicating a degree of muscle mass of the user and a fat index indicating a degree of fat mass of the user, and determine the nutritional ingredients based on the muscle index and the fat index.

13 Claims, 12 Drawing Sheets

(51) Int. Cl.
  *A23L 33/00* (2016.01)
  *G16H 70/60* (2018.01)
  *G16H 50/70* (2018.01)
  *A61B 5/00* (2006.01)

(52) U.S. Cl.
  CPC .......... *A61B 5/4872* (2013.01); *G16H 50/30* (2018.01); *G16H 50/70* (2018.01); *G16H 70/60* (2018.01); *A23V 2002/00* (2013.01)

(58) Field of Classification Search
  CPC ... A61B 5/4872; A23V 2002/00; G06Q 50/22
  USPC ........................................................ 705/2–3
  See application file for complete search history.

(56) References Cited

U.S. PATENT DOCUMENTS

| | | | | |
|---|---|---|---|---|
| 8,475,367 | B1* | 7/2013 | Yuen | G16H 50/30 177/4 |
| 2002/0040197 | A1* | 4/2002 | Sakata | A61B 5/4869 600/587 |
| 2003/0010791 | A1* | 1/2003 | Gentiluomo | G16H 20/13 221/92 |
| 2003/0216665 | A1* | 11/2003 | Masuo | A61B 5/4869 600/547 |
| 2003/0229275 | A1* | 12/2003 | Koyama | A61B 5/4869 600/300 |
| 2004/0131227 | A1* | 7/2004 | Bravomalo | G06Q 30/0269 382/100 |
| 2006/0081653 | A1* | 4/2006 | Boland | G16H 20/60 222/243 |
| 2011/0052764 | A1* | 3/2011 | Bulgin | A47J 31/404 700/285 |
| 2015/0132721 | A1* | 5/2015 | Domnich | G09B 19/0092 434/127 |
| 2015/0335608 | A1* | 11/2015 | Hughes | A61K 45/06 514/475 |
| 2016/0240101 | A1* | 8/2016 | Rak | G09B 5/02 |
| 2017/0098056 | A1* | 4/2017 | Reddy | G16H 20/13 |
| 2017/0224911 | A1* | 8/2017 | Dipierro | A61K 31/198 |
| 2018/0060530 | A1* | 3/2018 | Koh | G16H 10/60 |
| 2019/0147763 | A1* | 5/2019 | Nusbaum | A63B 24/0062 600/300 |

FOREIGN PATENT DOCUMENTS

| | | |
|---|---|---|
| JP | 2005-070853 A | 3/2005 |
| JP | 2006-026037 A | 2/2006 |
| JP | 2010-097621 A | 4/2010 |
| JP | 2011-204194 A | 10/2011 |
| JP | 2015-146168 A | 8/2015 |

OTHER PUBLICATIONS

Hackett, Training practices and ergogenic aids used by male bodybuilders, 2013, Journal of Strength and Conditioning Research, 27(6), 1609-1617 (Year: 2013).*

Leibel, Changes in energy expenditure resulting from altered body weight, 1995, N Engl J Med, Mar. 9;332(10):621-8 (Year: 1995).*

International Search Report issued in PCT/JP2019/010063; dated May 28, 2019.

Demling R H et al.; "Effect of a Hypocaloric Diet, Increased Protein Intake and Resistance Training on Lean Mass Gains and Fat Mass Loss in Overweight Police Officers"; Annals of nutrition and metabolism; Jan. 1, 2000; pp. 21-29; vol. 44; No. 1; Karger, CH. XP009087034.

* cited by examiner

TARGET BODY SHAPE SUPPLEMENTATION TABLE 132

| | I1 | Co1 | I2 | Co2 | |
|---|---|---|---|---|---|
| | FAT INDEX | SUPPLEMENTAL AMOUNT | MUSCLE INDEX | SUPPLEMENTAL AMOUNT | |
| | DIVERGENCE A | FAT ACCUMULATION INHIBITORY INGREDIENT | DIVERGENCE B | MUSCLE INCREASING INGREDIENT | CARBOHYDRATE |
| | +DIRECTION | 0 | −DIRECTION | 0 | 0 |
| | 0 ↑ $-Va_1$ | $(1 \times BM) + 1.0$ | 0 ↓ $+Va_1$ | $(2 \times BM) + 2$ | $(1 \times BM) + 1$ |
| | $-Va_1$ ↑ $-Va_2$ | $(2 \times BM) + 1.5$ | $+Va_1$ ↓ $+Va_2$ | $(4 \times BM) + 4$ | $(2 \times BM) + 2$ |
| | $-Va_2$ ↑ $-Va_3$ | $(3 \times BM) + 2.0$ | $+Va_2$ ↓ $+Va_3$ | $(6 \times BM) + 6$ | $(3 \times BM) + 3$ |
| | $-Va_3$ ↑ $-Va_4$ | $(4 \times BM) + 2.5$ | $+Va_3$ ↓ $+Va_4$ | $(8 \times BM) + 8$ | $(4 \times BM) + 4$ |

*FIG. 7*

LIFE STYLE DISEASE PREVENTION TABLE 133

| BIOMETRIC INDEX | BASAL METABOLIC RATE W (T1) | | VISCERAL FAT MASS X (T2) | | BONE MASS Y (T3) | | BODY WATER BALANCE Z (T4) | |
|---|---|---|---|---|---|---|---|---|
| NUTRITIONAL INGREDIENT | METABOLISM ACTIVATING INGREDIENT BLOOD CIRCULATION PROMOTING INGREDIENT | | ANTIOXIDANT INGREDIENT LIPOLYTIC INGREDIENT LIPID METABOLISM PROMOTING INGREDIENT | | BONE FORMING INGREDIENT BONE METABOLISM SUPPLEMENTAL INGREDIENT | | EXCRETION PROMOTING INGREDIENT BLOOD FLOW SMOOTHING INGREDIENT | |
| ADDITION AMOUNT | DETERMINATION RESULT | INGREDIENT AMOUNT | DETERMINATION RESULT | INGREDIENT AMOUNT | DETERMINATION RESULT | INGREDIENT AMOUNT | DETERMINATION RESULT | INGREDIENT AMOUNT |
| | HIGH | A1 (SMALL) | SMALL | B1 (SMALL) | LARGE | C1 (SMALL) | BETTER | D1 (SMALL) |
| | STANDARD | A2 (MEDIUM) | STANDARD | B2 (MEDIUM) | STANDARD | C2 (MEDIUM) | STANDARD | D2 (MEDIUM) |
| | LOW | A3 (LARGE) | LARGE | B3 (LARGE) | SMALL | C3 (LARGE) | WORSE | D3 (LARGE) |

FIG. 9

INGREDIENT DETERMINING DEVICE, INGREDIENT DETERMINING METHOD AND NON-TRANSITORY COMPUTER-READABLE RECORDING MEDIUM

TECHNICAL FIELD

The present invention relates to an ingredient determining apparatus, an ingredient determining method and a non-transitory computer-readable recording medium for determining nutritional ingredients in food provided to a user.

BACKGROUND ART

JP2004-272618A discloses a system in which, when a user's symptom is input to an input means, the system refers to data indicating a nutrition required for each symptom and data indicating a nutrition included in each supplement and determines a supplement which can improve the user's symptom.

However, the inventors have recognized that, since the above-described systems are configured to determine the supplement according to the subjective symptom or purpose of the user, even for users whose required nutritional ingredients for their body are different, a similar supplement is provided if they have a similar idea or feeling. The inventors have recognized that such systems may provide a food having similar nutritional ingredients to users having different health conditions.

The present invention has been made in view of the above problems, and an object thereof is to provide an ingredient determining apparatus, an ingredient determining method and a non-transitory computer-readable recording medium for accurately determining nutritional ingredients according to a health condition of a user.

SUMMARY OF INVENTION

According to an aspect of present invention, an ingredient determining apparatus configured to determine nutritional ingredients in food provided for a user, includes a processor configured to obtain a muscle index indicating a degree of muscle mass of the user and a fat index indicating a degree of fat mass of the user, and determine means for determining the nutritional ingredients based on the muscle index and the fat index.

According to this aspect, by using two indexes that are less correlated with each other among body compositions to which the health condition of the user is easily reflected, the nutritional ingredients can be accurately determined according to the health condition of the user

BRIEF DESCRIPTION OF DRAWINGS

FIG. 7 is a conceptual diagram showing an example of a target body shape supplementation table for specifying the supplemental amounts of the nutritional ingredients based on a target vector from the body shape to the target body shape of the user.

FIG. 9 is a diagram illustrating an example of a lifestyle disease prevention table for identifying the nutritional ingredients for preventing a health risk in the third embodiment.

DESCRIPTION OF EMBODIMENTS

Embodiments of the present invention will be described below referring to the attached drawings.

First Embodiment

Figure 1:
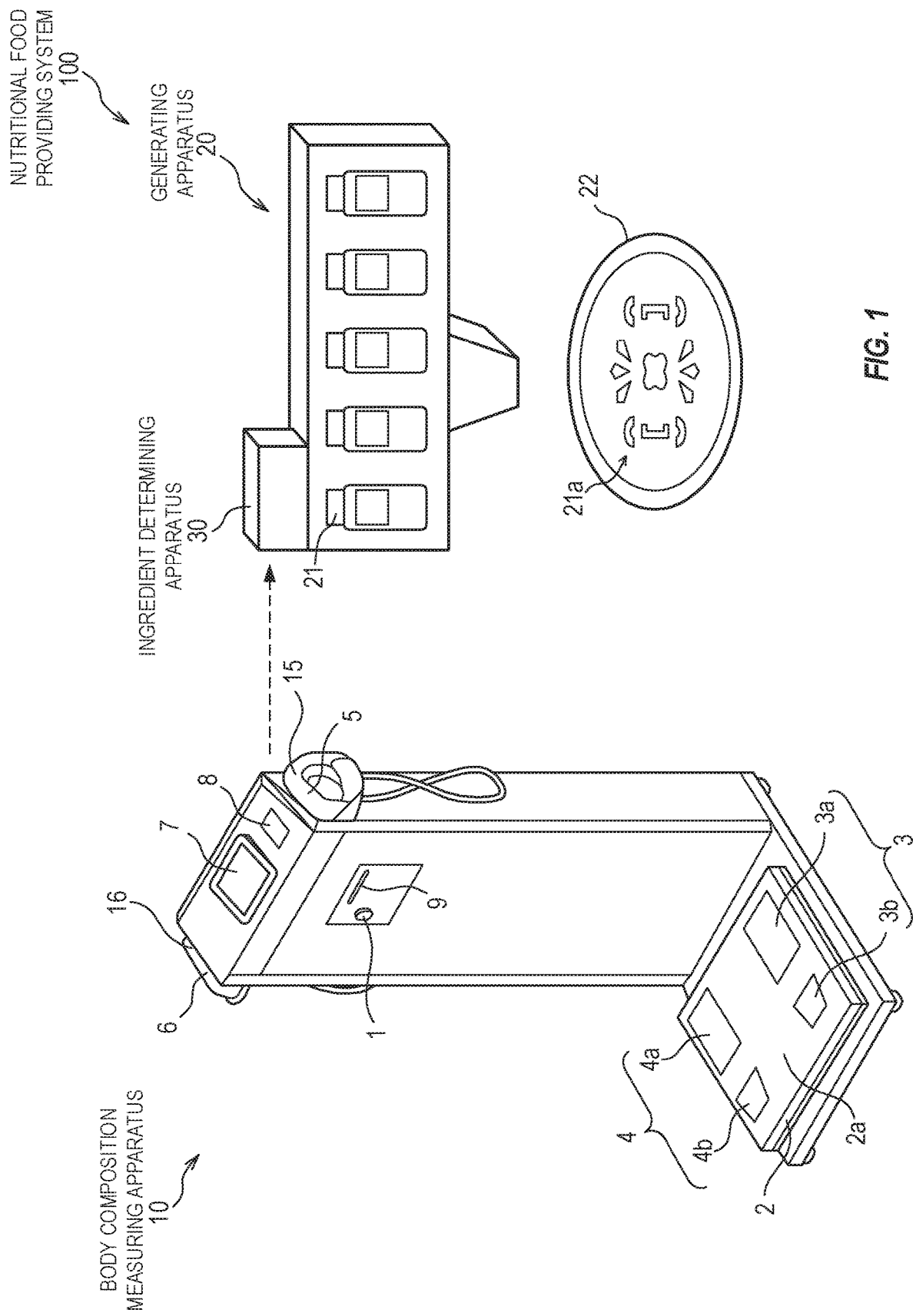
FIG. 1 is a schematic diagram showing a nutritional food providing system according to the first embodiment.

FIG. 1 is a schematic view illustrating an appearance of a nutritional food providing system 100 of the first embodiment of the present invention.

The nutritional food providing system 100 is a system that provides a food obtained by blending one or a plurality of nutritional ingredients according to a health condition of a user. Examples of food obtained by blending the nutritional ingredients include vegetable salads, snacks, juice, and the like, and in the present embodiment, a supplement which is a nutritional supplementary food is provided as the food.

The nutritional food providing system 100 is located, for example, in a pharmacy, a fitness club, a public bathhouse, and the like. The nutritional food providing system 100 includes a body composition measuring apparatus 10 for measuring a body composition of the user, and a generating apparatus 20 for generating the supplement based on a measurement result from the body composition measuring apparatus 10.

The body composition measuring apparatus 10 includes a power switch 1 for powering the body composition measuring apparatus 10, a body weight measuring unit 2 for measuring weight of the user on a placing surface 2a of the body composition measuring apparatus 10, and an electrode portion 3 and an electrode portion 4 for measuring an organism impedance of the user located on the placing surface 2a of the body composition measuring apparatus 10. The body composition measuring apparatus 10 further includes a handle 15 and a handle 16 to be gripped by the user, an electrode portion 5 and an electrode portion 6 located on the handle 15 and the handle 16, respectively, a display operation device 7, a communication device 8 and a printer 9.

On the placing surface 2a of the body composition measuring apparatus 10, the electrode portion 3 in contact with the right foot of the user on the placing surface 2a and the electrode portion 4 in contact with the left foot of the user on the placing surface 2a are located, respectively. In addition, the handle 15, which the user can grip with the right hand, and the handle 16, which the user can grip with the left hand, are each provided on the body composition measuring apparatus 10. The handle 15 is arranged with the electrode portion 5 that contacts the right hand of the user when the user grips with the right hand, and the handle 16 is arranged with the electrode portion 6 that contacts the left hand of the user when the user grips with the left hand. Each of the electrode portions 3, 4, 5 and 6 include two electrodes. One of the two electrodes is a current application electrode (hereinafter, also referred to as a current electrode.) and the other one is a voltage measuring electrode (hereinafter, also referred to as a voltage electrode).

The body composition measuring apparatus 10 determines two current electrodes among the four current electrodes by a current applying path determination unit (not shown), and, by a current application unit (not shown), applies a current between the two current electrodes determined by the current applying path determination unit. As a result, a current flows in a path in the body of the user formed by the two current electrodes determined by the current applying path determination unit.

Then, the body composition measuring apparatus 10 determines two voltage electrodes of the four voltage electrodes by a measuring electrode determination unit (not shown), a voltage detector (not shown) detects a voltage drop between the two voltage electrodes determined by the measuring electrode determination unit. At this time, the measuring electrode determination unit determines the two voltage electrodes such that at least a part of the path in the body of the user formed by the two current electrodes determined by the current applying path determination unit is included in the path in the body of the user formed by the two voltage electrodes.

The body composition measuring apparatus 10, with the impedance calculating unit (not shown), calculates the impedance from the current value output by the current applying unit and the voltage value detected by the voltage detecting unit. Namely, the body composition measuring apparatus 10 calculates the impedance of the part of the user's body where the path formed by the two current electrodes and the path formed by the two voltage electrodes overlap each other.

Thus, the body composition measuring apparatus 10 uses the current applying path determination unit and the measuring electrode determination unit to determine the appropriate two current electrodes and two voltage electrodes to measure the impedances of an arbitrary part in the user's body. Then, the body composition measuring apparatus 10 calculates the impedances of the arbitrary part using the current application unit and the voltage detecting unit.

The display operation device 7 receives an input of basic biometric information of the user by the input manipulation of the user, and displays the measurement result of the body composition to the user. The basic biometric information includes, for example, height, age, and sex of the user. The display operation device 7 is configured by, for example, a touch panel type or a push-button type liquid crystal display device.

The communication device 8 performs communication with the generating apparatus 20 or an external terminal (not shown). For example, the communication device 8 communicates with the generating apparatus 20 or an external terminal via a short-range radio communication, a mobile phone network, and the like. The communication device 8 of the present embodiment transmits the measurement result of the user to the generating apparatus 20, and receives biometric data including the previous measurement result of the user and the like from the external terminal.

In this manner, the body composition measuring apparatus 10 measures the weight of the user, measures the organism impedances of the right leg, left leg, right arm and left arm of the user, and applies these measurement values to a predetermined regression line or a calculation formula to calculate the body composition of the user.

The body composition of the user includes fat rate, fat mass, fat free mass, visceral fat mass, visceral fat level, visceral fat area, subcutaneous fat mass, muscle mass, bone mass, body water percentage, body water content, intracellular fluid volume, and extracellular fluid volume of the whole body and various parts.

The body composition measuring apparatus 10 transmits the body composition data indicating the calculated values of the body composition to the generating apparatus 20 as the measurement result of the user. However, the body composition measuring apparatus 10 may transmit the BMI which is a body mass index, together with a basal metabolic rate calculated from the above-described body composition.

The generating apparatus 20 includes a plurality of containers 21. Each of the containers 21 contains a supplement material. The generating apparatus 20 produces a supplement 21a by extracting the supplement material by an arbitrary amount from each of the containers 21 and blending the extracted supplement materials. By accommodating the supplement material having different nutritional ingredient for each of the containers 21, the generating apparatus 20 can adjust the nutritional ingredients contained in the supplement 21a.

In this embodiment, the generating apparatus 20 includes an ingredient determining apparatus 30 for determining the nutritional ingredients required for the user's body in accordance with the health condition in the user's body, and places the supplement 21a composed of one or more supplement materials on a dish 22 according to the nutritional ingredients determined in the ingredient determining apparatus 30.

For example, the generating apparatus 20 stores the nutritional ingredient data relating to the supplement materials. In the nutritional ingredient data, for each of the containers 21, the ingredients contained in the supplement material and the content per unit weight of the supplement material for this ingredient are shown, respectively. In this case, upon receiving an instruction from the ingredient determining apparatus 30 for the nutritional ingredients and the ingredient amounts thereof, the generating apparatus 20 refers the nutritional ingredient data, extracts the required amount of the supplement material from each of the five containers 21 and generates the supplement 21a by blending them.

Alternatively, the nutritional ingredient data described above may be such that only the ingredients contained in the supplement material are shown for each of the containers 21. In this case, upon receiving the nutritional ingredient instruction from the ingredient determining apparatus 30, the generating apparatus 20 refers the nutritional ingredient data, extracts a certain quantity of the supplement material having the indicated nutritional ingredients from among the five containers 21. The ingredient determining apparatus 30 then generates the supplement 21a by blending the extracted supplement materials.

Figure 2:
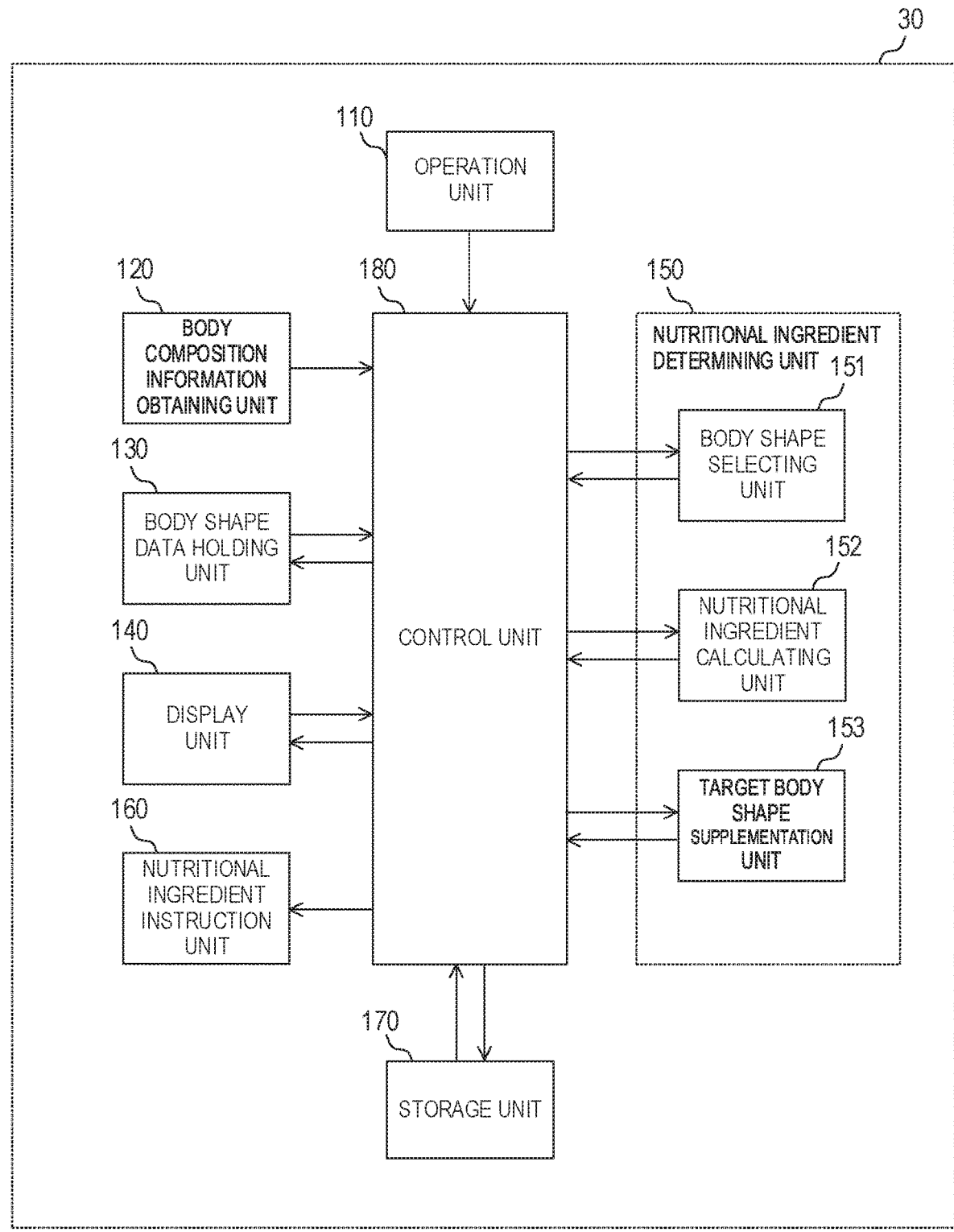
FIG. 2 is a block diagram showing an example of a functional configuration of an ingredient determining apparatus included in a generating apparatus.

FIG. 2 is a block diagram showing an example of a functional configuration of the ingredient determining apparatus 30 according to the present embodiment.

The ingredient determining apparatus 30 is a computer that executes an ingredient determination process for determining nutritional ingredients to be supplied to the user's body and the ingredient amounts thereof based on the body composition data of the user. The ingredient determination process executed by the ingredient determining apparatus 30 is hereinafter referred to as a supplement determination process.

The ingredient determining apparatus 30 includes an operation unit 110, a body composition information obtaining unit 120, a body shape data holding unit 130, a display unit 140, a nutritional ingredient determining unit 150, a nutritional ingredient instruction unit 160, a storage unit 170, and a control unit 180.

The operation unit 110 is constituted by touch sensors, push buttons, dials, and the like, and constitutes a receiving means for receiving user inputs. The operation unit 110 receives an operation of turning on or off the power switch of the generating apparatus 20, or receives an operation of directly specifying the supplement 21a.

The operation unit 110 of the present embodiment receives an instruction from the user to execute the supplement determination process. The operation unit 110 can also receive an operation for inputting the basic biometric information or the body composition data required for the supplement determination process. In addition, the operation unit 110 receives an input operation of the target body shape information indicating the target body shape targeted by the user. As for the target body shape information, the information received by the body composition measuring apparatus 10 may be received from the body composition information obtaining unit 120.

The body composition information obtaining unit 120 obtains the body composition data indicating the body compositions such as fat, bone, muscle, and water content of the user in order to identify a lifestyle that is a user's daily lifestyle habit. The body composition information obtaining unit 120 of the present embodiment constitutes an obtaining means for obtaining, among the body compositions of the user, a fat index indicating the degree of the user's fat and a muscle index indicating the degree of the user's muscle mass.

The above-mentioned fat index and muscle index are used to specify the body shape of the user. The fat index is an index indicating the percentage of the fat mass in the body, and includes, for example, either one of fat rate, fat mass and subcutaneous fat mass of the whole body or each part, or either one of visceral fat mass, visceral fat level and visceral fat area. In the present embodiment, the whole body fat rate is used as the fat index.

The muscle index is an index indicating the muscle mass or an index that correlates with the muscle mass, and is an index that is less correlated with the fat index. The muscle index include, for example, muscle mass, fat free mass or bone mass, or BMI or basal metabolic rate of the whole body or each part. In the present embodiment, as the muscle index, the muscle mass score obtained by dividing the whole body muscle mass by the height is used.

The body composition information obtaining unit 120 receives the body composition information of the user from the body composition measuring apparatus 10, a portable terminal held by the user, an external device such as a management server that manages body composition information of the user, or the like. The body composition information obtaining unit 120 may obtain the user's body composition information from the operation unit 110, or may obtain the user's body composition information from an external device such as a USB (Universal Serial Bus) memory.

The body composition information obtaining unit 120 may receive the weight of the user and the organism impedance of each part of the user from the body composition measuring apparatus 10 and generate the body composition information based on these measurements. As described above, the body composition information obtaining unit 120 is constituted by a communication circuit, an interface circuit, a body composition calculation circuit, and the like.

The body shape data holding unit 130 holds the body shape data that indicates the relation between the value of the fat index and the value of the muscle index for each predetermined body shape type. Each body shape type shown in the body shape data is associated with the nutritional ingredients and the ingredient amounts thereof required for healthily managing body shape of the user belonging to the body shape type.

Managing the body shape healthily as mentioned above means changing the user's body shape in such a way that the likelihood of harming health is reduced, if the body shape is a shape that is likely to harm health (e.g. too much fat or muscle, or too little fat or muscle). If the user's body shape is a shape that is less likely to harm health, managing the body shape healthily means maintaining the body shape.

For example, the body shape data holding unit 130 holds the body shape data generated for each age and for each sex. This allows the body shape of the user to be classified into an appropriate body shape type appropriate for their age and sex. The details of the body shape type will be described later with reference to FIG. 3 and the details of the nutritional ingredients required for managing the body shape of the user will be described later with reference to FIG. 4.

The display unit 140 is constituted by, for example, a touch panel type or a push button type liquid crystal display device or the like. The display unit 140 displays supplements that can be provided to the user, or displays a picture for selecting whether the above-described supplement determination process is necessary or not.

For example, when the operation unit 110 receives an operation for instructing to execute the supplement determination process operation, based on the body composition information of the user, the display unit 140 displays the body shape of the user or the body shape type to which the body shape of the user belongs among the predetermined body shape types. Further, when the operation unit 110 receives the input operation of the target body shape information, the display unit 140 displays the target body shape type targeted by the user or the body shape type to which the target body shape belongs among the predetermined body shape types based on the target body shape information.

The nutritional ingredient determining unit 150 constitutes a determining means for determining the nutritional ingredients required for the user's body based on the fat index and the muscle index specifying the body shape of the user. Specifically, the nutritional ingredient determining unit 150 determines the types of nutritional ingredients only or both of the types of nutritional ingredients and the ingredient amounts thereof required for the user's body based on the fat index and the muscle index of the user.

The nutritional ingredient determining unit 150 of the present embodiment calculates the nutritional ingredients required for managing the body shape of the user based on the fat index and the muscle index of the user. The nutritional ingredient determining unit 150 includes a body shape selecting unit 151, a nutritional ingredient calculating unit 152, and a target body shape supplementation unit 153.

The body shape selecting unit 151 selects a body shape type to which the body shape of the user belongs from among the predetermined body shape types based on the fat index and the muscle index of the user. When the body shape selecting unit 151 of the present embodiment obtains the fat index and the muscle index of the user from the body composition information obtaining unit 120, it refers to the body shape data holding unit 130 and selects the body shape type associated with the obtained values as the body shape of the user.

The nutritional ingredient calculating unit 152 refers to the body shape data holding unit 130 based on the body shape type of the user selected by the body shape selecting unit 151, and calculates the nutritional ingredients and the ingredient amounts thereof associated with the body shape type of the user. The nutritional ingredient calculating unit 152 outputs the ingredient determining information indicating the ingredient amounts of the nutritional ingredients to the nutritional ingredient instruction unit 160.

When the target body shape supplementation unit 153 obtains the target body shape information of the user from the operation unit 110, it supplements the nutritional ingredients required for realizing the change to the target body shape based on the target body shape information. In the present embodiment, the target body shape supplementation unit 153 obtains the divergence between the body shape and the target body shape of the user based on the target body shape information, and supplements the nutritional ingredients and the ingredient amounts thereof required for reducing the divergence based on the divergence. The target body shape supplementation unit 153 outputs the nutritional supplemental information indicating the ingredient amounts of the nutritional ingredients to be supplemented to the nutritional ingredient instruction unit 160 as the ingredient determining information.

Based on the types of the nutritional ingredients shown in the ingredient determining information from the nutritional ingredient determining unit 150, the nutritional ingredient instruction unit 160 selects the containers 21 containing the supplement materials having corresponding nutritional ingredients. Additionally, the nutritional ingredient instruction unit 160 instructs the number of supplement materials for each of the selected containers 21 based on the ingredient amounts of the nutritional ingredients shown in the ingredient determining information. As a result, as shown in FIG. 1, the supplement 21a generated by the generating apparatus 20 is provided on the dish 22.

The storage unit 170 includes a non-volatile memory (ROM; Read Only Memory) and a volatile memory (RAM; Random Access Memory). The storage unit 170 contains a control program for controlling the ingredient determining apparatus 30. That is, the storage unit 170 is a recording medium that stores a program for realizing the functions of the present embodiment.

The control unit 180 includes a central processing unit (CPU), an input/output interface, and buses that interconnect them. The control unit 180 reads out the control program stored in the storage unit 170 and causes the CPU to execute it, thereby controlling the various parts of the ingredient determining apparatus 30 through the input/output interface.

The control unit 180 controls each of the operation unit 110, the body composition information obtaining unit 120, the body shape data holding unit 130, the display unit 140, the nutritional ingredient determining unit 150, the nutritional ingredient instruction unit 160 and the storage unit 170 as described above. The CPU that constitutes the control unit 180 may perform the functions of the various parts of the ingredient determining apparatus 30.

The processings of the respective parts other than the control unit 180 may be fully or partially realized by a dedicated hardware such as an ASIC (application specific integrated circuit). In this manner, the processing of the respective parts of the ingredient determining apparatus 30 may be implemented by software (program) or hardware, and may be implemented by the combination of software and hardware.

Next, based on the fat index and the muscle index of the user, a method for determining the user's body shape type will be described with reference to FIG. 3.

Figure 3:
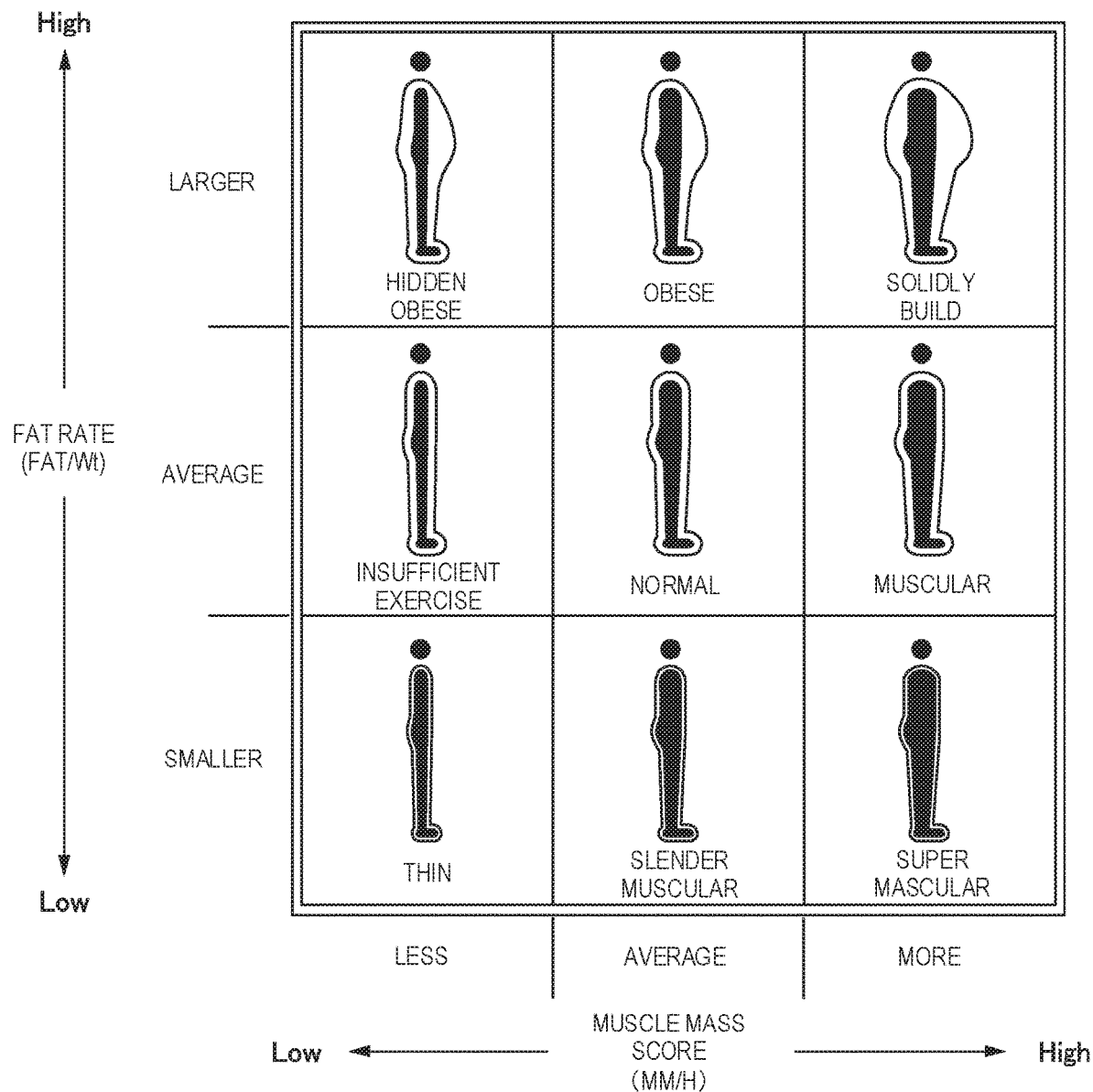
FIG. 3 is a schematic diagram showing an example of classification of body shape types specified by a muscle index and a fat index of a user.

FIG. 3 is a schematic diagram showing an example of the body shape data held by the body shape data holding unit 130.

In this case, the abscissa represents the muscle mass score (MM/H) as the muscle index, and the ordinate represents the fat rate (FAT/Wt) as the fat index. The muscle mass score is the ratio of the muscle mass MM (Muscle Mass to the height H (Height) and the fat rate is the ratio of the fat mass (FAT) of the whole body to the body weight Wt (Weight).

As shown in FIG. 3, the body shape of the user is classified by the fat rates. In this case, three ranges of "average" range, a "smaller" range, and "larger" range are set for the fat rate. The range of the "average" is predetermined based on the statistical or group data of the fat rates of a plurality of persons.

Further, in the present embodiment, in addition to the fat rate, the body shapes of the user are classified by the muscle mass scores. In this embodiment, three ranges are set for the muscle mass scores like the fat rate: a range of "average", a range of "less" and a range of "more" with respect to the range of "average". The "average" range of the muscle mass score is predetermined based on the statistical or group data of the muscle mass score of a plurality of persons.

The body shape types indicating "thin", "slender muscular" and "super muscular" are associated with the body shape data in the respective ranges of "less", "average" and "more" of the muscle mass score in which the range of the fat rate is "smaller".

Similarly, the body shape types indicating "insufficient exercise", "normal", and "muscular" are associated with the body shape data in the respective ranges of the muscle mass score in which the range of the fat rate is "average". Further, the body shape types indicating "hidden obese", "obese", and "solidly built" are associated with the body shape data in the respective ranges of the muscle mass score in which the range of the fat rate is "larger".

Therefore, the body shape selecting unit 151 can select the body shape type corresponding to the values of the fat rate and the muscle mass score of the user from among the nine body shape types by referring to the above-mentioned body shape data.

In this manner, by classifying the body shape of the user using the muscle mass score that is less correlated with the fat rate in addition to the fat rate of the body in which the effects of lifestyle are easily reflected, the body shape of the user becomes less biased to one body shape type, and fine classification can be realized.

Next, a method for determining the nutritional ingredients required for the user's body will be described in FIGS. 4 and 5.

Figure 4:
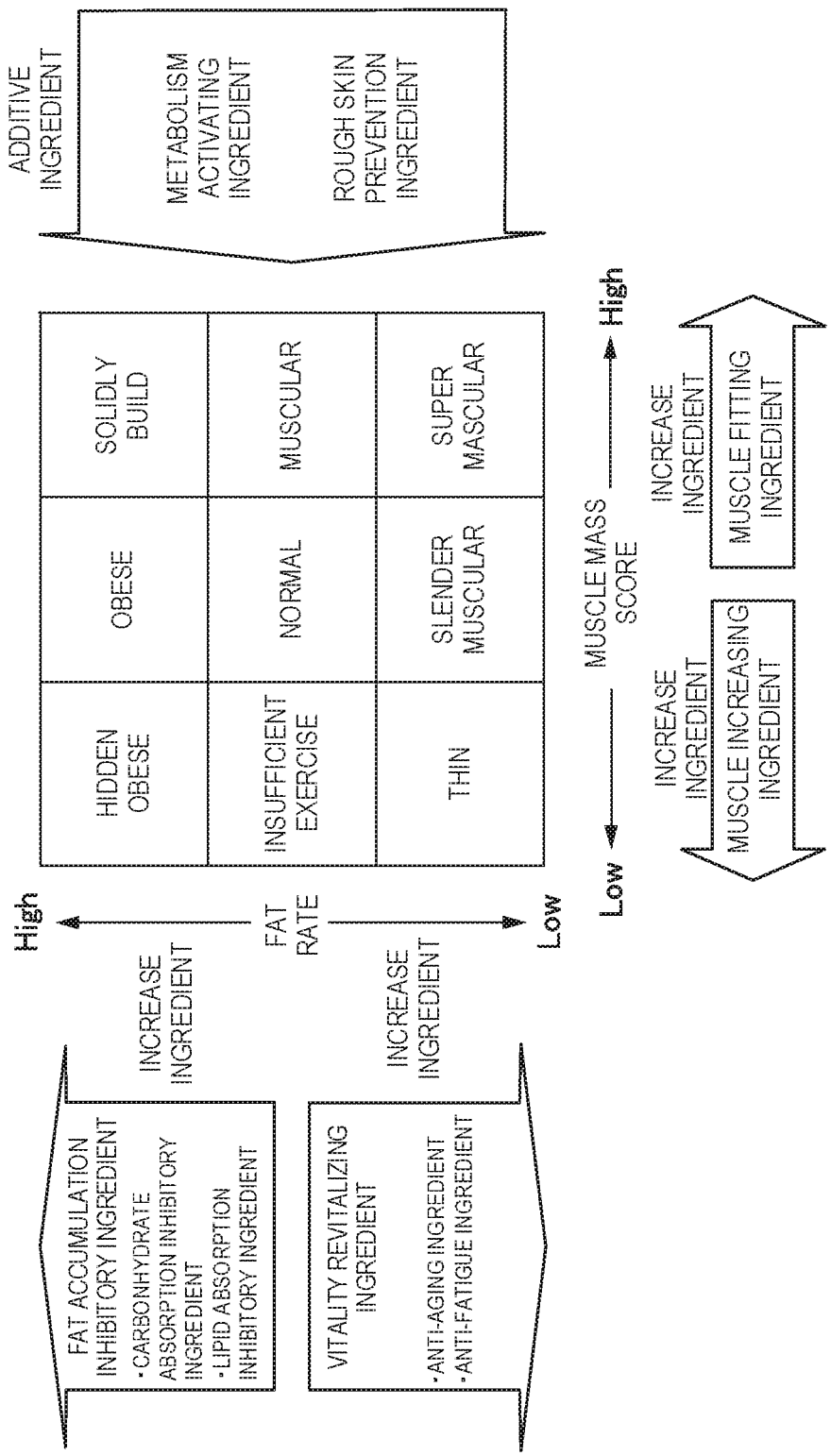
FIG. 4 is a conceptual diagram showing an example of nutritional ingredients required for managing a body shape for each body shape type.

FIG. 4 is a diagram for explaining the trends of the nutritional ingredients and the ingredient amounts thereof required for healthy control of the body shape of the user for each body shape type shown in FIG. 3.

First, the nutritional ingredients and the ingredient amounts thereof selected according to the value of the fat rate will be described.

If the value of the fat rate of the user falls within the "larger" range shown in FIG. 3, a fat accumulation inhibitory ingredient shown in FIG. 4 is selected to inhibit the increase in the fat rate. As the fat rate becomes large, the ingredient amount of the selected fat accumulation inhibitory ingredient is increased.

The fat accumulation inhibitory ingredient described above is the nutritional ingredient required for inhibiting (obstructing) the accumulation of fat. The fat accumulation inhibitory ingredient includes, for example, of at least one nutritional ingredient of a carbohydrate absorption inhibitory ingredient which inhibits absorption of carbohydrate and a lipid absorption inhibitory ingredient which inhibits absorption of lipid. The carbohydrate absorption inhibitory ingredient and lipid absorption inhibitory ingredient mainly include dietary fiber and the like. As the fat accumulation inhibitory ingredient, a fat burning ingredient which promotes burning of fat may be included, and examples of the fat burning ingredient include allicin and the like.

If the value of the fat rate of the user falls within the "average" range shown in FIG. 3, in order to healthily maintain the body shape of the user belonging to this range, the metabolism activating ingredient and the rough skin prevention ingredient shown in FIG. 4 are selected. The metabolism activating ingredient is a nutritional ingredient required for activating metabolism, and examples thereof include L-carnitine and the like. The rough skin prevention ingredient is a nutritional ingredient required for preventing rough skin, and examples thereof include Vitamin C and the like.

If the value of the fat rate falls within the "smaller" range shown in FIG. 3, in order to relieve symptoms that are likely to occur in the user belonging to this range, the vitality revitalizing ingredient shown in FIG. 4 is selected. As the fat rate becomes small, the ingredient amount of the selected vitality revitalizing ingredient is increased.

The above-mentioned vitality revitalizing ingredient is a nutritional ingredient required for inhibiting the decline in vitality, and is a nutritional ingredient in which people with little fat mass tend to lack especially. The vitality revitalizing ingredient may include, for example, a nutritional ingredient of at least one of an anti-fatigue ingredient which reduces fatigue and an anti-aging ingredient for maintaining youthful. Examples of the anti-fatigue ingredient include citric acid, vitamin C, and vitamin B complex, and examples of the anti-aging ingredient include vitamin E and coenzyme Q10.

In the examples shown in FIG. 4, as the fat rate value of the user increases from the standard value determined by the mean value, the median value, the mode value, or the like of the human fat rate, the fat accumulation inhibitory ingredient is increased, and as the fat rate value of the user decreases from the standard value, the anti-aging ingredient and the anti-fatigue ingredient are increased. In addition, the rough skin prevention ingredient and the anti-aging ingredient are added regardless of the fat rate value of the user.

In this manner, based on the value of the fat rate of the user, the nutritional ingredients required for managing the body shape control of the user and the ingredient amounts thereof are determined from among the fat accumulation inhibitory ingredient, the metabolism activating ingredient, the rough skin prevention ingredient, the anti-aging ingredient and the anti-fatigue ingredient.

Next, the nutritional ingredients determined according to the value of the muscle mass score and the ingredient amount thereof will be described.

If the muscle mass score of the user falls within the "less" range shown in FIG. 3, in order to inhibit further reduction in the muscle mass of the user belonging to this range, a muscle increasing ingredient shown in FIG. 4 is selected. As the muscle mass score becomes small, the ingredient amount of the selected muscle increasing ingredient is increased. The muscle increasing ingredient referred to herein is a nutritional ingredient required for increasing the muscle mass, and mainly includes leucine and the like.

If the muscle mass score of the user falls within the range of "more" shown in FIG. 3, in order to healthily keep the muscles of the user belonging to this range, a muscle fitting ingredient shown in FIG. 4 is selected. As the muscle mass score becomes large, the ingredient amount of the selected muscle fitting ingredient is increased.

The above-mentioned muscle fitting ingredient is a nutritional ingredient required for keeping muscles healthy, and the muscle fitting ingredient contains a metabolism promoting ingredient and the like that promotes metabolism of muscle, and the metabolism promoting ingredient mainly includes vitamins and the like. The metabolism of the muscle as used herein refers to repairing wound, i.e., promoting repairs, when a muscle fiber is destroyed by training or the like and a minute wound occurs in the muscle fiber. Repeated destruction and repair of muscle fibers like this leads to muscle building (muscle hypertrophy).

If the muscle mass score of the user falls within the "average" range shown in FIG. 3, in order to maintain the muscle mass of the user belonging to this range, the ingredient amount of the muscle fitting ingredient is adjusted according to the muscle mass score. Specifically, as the muscle mass score becomes large, the ingredient amount of the muscle fitting ingredient is increased, and as the muscle mass score becomes small, the ingredient amount of the muscle fitting ingredient is decreased.

In this manner, the nutritional ingredients and the ingredient amounts thereof required for managing the body shape of the user are determined from the muscle increasing ingredient and the muscle fitting ingredient based on the value of muscle mass score of the user.

Figure 5:
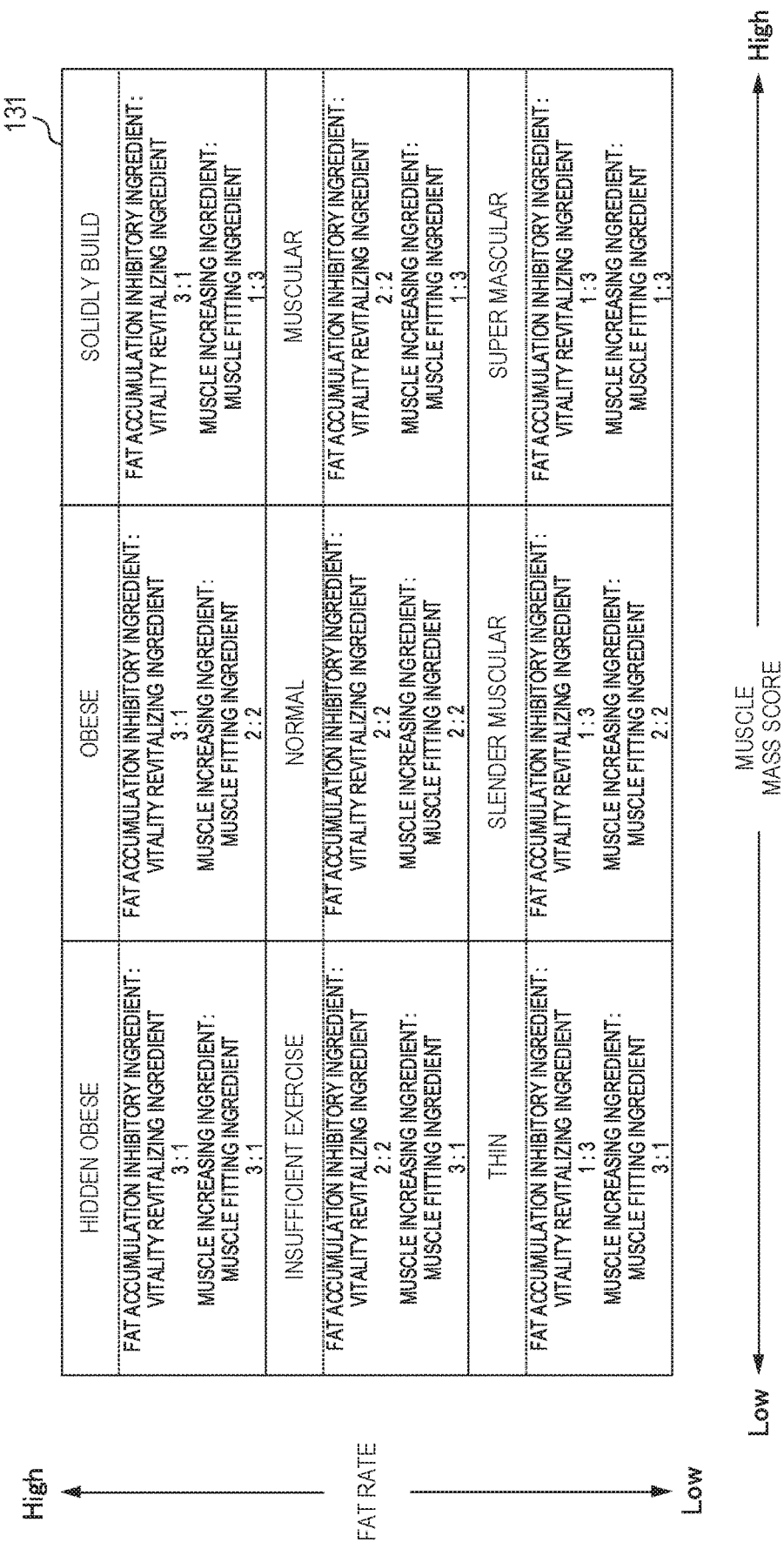
FIG. 5 is a conceptual diagram illustrating an example of a body shape management table for specifying a ratio of the nutritional ingredients associated with each body shape type.

FIG. 5 is a diagram showing an example of the body shape management table 131 showing the relation between the body shape type of the user and the ingredient amounts of the nutritional ingredients.

As shown in FIG. 5, in the body shape management table 131, the ratios of the nutritional ingredients required for managing the body shape of the user belonging to the body shape type to the ingredient amounts thereof are associated with each of the body shape types shown in the body shape table. The ratio of "2" means that the ingredient amount is normal, the ratio of "3" means that the ingredient amount is greater than normal and the ratio of "1" means that the ingredient amount is less than normal.

For example, for the "hidden obese" in the body shape management table 131, the ratio of the fat accumulation inhibitory ingredient to the vitality revitalizing ingredient is set to "3:1" for fat, and the ratio of the muscle increasing ingredient to the muscle fitting ingredient is also set to "3:1" for muscle.

On the other hand, for the "normal" in the body shape management table 131, the ratio of fat accumulation inhibitory ingredient to the vitality revitalizing ingredient is set to "2:2" for fat, and the ratio of the muscle increasing ingredient to the muscle fitting ingredient is also set to "2:2" for muscle.

Thus, in the body shape management table 131, as the fat rate of the user becomes large, the ingredient amount of the fat accumulation inhibitory ingredient increases and the ingredient amount of the vitality revitalizing ingredient decreases. On the other hand, as the fat rate of the user becomes small, the ingredient amount of the fat accumulation inhibitory ingredient decreases and the ingredient amount of the vitality revitalizing ingredient increases.

In addition, as the muscle mass score of the user becomes large, the ingredient amount of the muscle fitting ingredient increases and the ingredient amount of the muscle increasing ingredient decreases. On the other hand, as the muscle mass score of the user become small, the ingredient amount of the muscle fitting ingredient decreases and the ingredient amount of the muscle increasing ingredient increases.

Therefore, by using the body shape management table 131, the nutritional ingredient calculating unit 152 can appropriately calculate the ingredient amounts of the nutritional ingredients required for managing the body shape of the user in accordance with the body shape type of the user.

For example, when the nutritional ingredient calculating unit 152 determines that the body shape of the user belongs to the "insufficient exercise" type, for the nutritional ingredients associated with the "insufficient exercise" type in the body shape management table 131, the ratio of the fat accumulation inhibitory ingredient to the vitality revitalizing ingredient and the ratio of the muscle increasing ingredient to the muscle fitting ingredient are specified.

In the case of FIG. 5, since the ratio of the fat accumulation inhibitory ingredient to the vitality revitalizing ingredient is "2:2", the nutritional ingredient calculating unit 152 sets predetermined basic quantities as the ingredient amounts of both. Further, since the ratio of the muscle increasing ingredient to the muscle fitting ingredient is "3:1", the nutritional ingredient calculating unit 152 calculates a value obtained by multiplying the predetermined basic amount by 1.5 as the ingredient amount of the muscle increasing ingredient, and calculates a value obtained by multiplying the basic amount by 0.5 as the ingredient amount of the muscle fitting ingredient.

In this embodiment, using the body shape management table 131, the fat accumulation inhibitory ingredient, the vitality revitalizing ingredient, the muscle increasing ingredient, and the muscle fitting ingredient are selected as the nutritional ingredients required for managing the body shape, but a metabolism activating ingredient and a rough skin prevention ingredient may be added for any of the body shapes. Alternatively, the metabolism activating ingredient and the rough skin prevention ingredient may be blended as main ingredients to the selected nutritional ingredients.

Next, the operation and effect of the first embodiment will be described in detail.

According to the first embodiment, the ingredient determining apparatus 30 for determining the nutritional ingredients to be blended to the food includes the body composition information obtaining unit 120 as an obtaining means for obtaining the muscle index indicating the degree of the muscle mass of the user and the fat index indicating the degree of the fat mass of the user.

Here, examples of the food to which the nutritional ingredients are blended include supplements, drinks, snacks, and vegetable salads. Further, examples of the muscle index include BMI, muscle mass of a whole body or a particular body part, ratio of the muscle mass to height, bone mass, fat free mass or basal metabolic rate of a whole body or a particular body part, and the like. Fat index may include, for example, fat rate of the whole body or a particular body part, the ratio of the fat mass to the body weight, or the like.

The ingredient determining apparatus 30 includes the nutritional ingredient determining unit 150 as a determining means for determining the nutritional ingredients required for user's body based on the obtained values of the muscle index and the fat index of the user.

The above-mentioned muscle index and fat index are objective index representing health condition of the main elements constituting the body, and by using them, it is possible to accurately determine nutritional ingredients objectively required for the body of the user while removing the subjective view of the user.

Further, the muscle index and the fat index are indexes that easily reflect the effects of the user's lifestyle, and by using them, the health condition in the body formed over a long period of time can be identified. Therefore, it is possible to understand the fundamental symptoms in the body that reflect user's lifestyle, and thus it is possible to provide the nutritional ingredients that are highly important to the user's body.

In addition, the muscle index and the fat index of the user obtained by the body composition information obtaining unit 120 are not correlated with each other, and thus the health condition in the body can be understood in detail from different perspectives. Therefore, the nutritional ingredients required for user's body can be finely determined.

As described above, according to the present embodiment, the nutritional ingredients can be accurately determined in accordance with the health condition of the user by using the two indexes that are less correlated with each other among the body compositions to which the health condition in the body of the user is easily reflected.

According to the present embodiment, the nutritional ingredient determining unit 150 calculates the nutritional ingredients required for managing the body shape of the user based on the muscle index and the fat index of the user. As described above, by specifying the body shape of the user on the basis of the muscle index and the fat index of the user, the nutritional ingredients required for managing the body shape of the user is decided, and therefore, it is possible to blend the nutritional ingredients considering the lifestyle of the user to the food. The finer blending can be realized by changing the ingredient amounts of the decided nutritional ingredients in accordance with the body shape of the user.

According to this embodiment, the ingredient determining apparatus 30 is further provided with the body shape data holding unit 130 as the holding means for holding the nutritional ingredients required for managing the body shape of the user in association with each of the predetermined body shape types as shown in FIG. 3.

The nutritional ingredient determining unit 150 includes the body shape selecting unit 151 as a selecting means for selecting the body shape type to which the body shape of the user belongs from among the predetermined body shape types based on the muscle index and the fat index of the user. The nutritional ingredient determining unit 150 further includes the nutritional ingredient calculating unit 152 as a calculating means for calculating the nutritional ingredients associated with the body shape type of the user by referring to the body shape data holding unit 130 based on the body shape type of the user selected by the body shape selecting unit 151.

The body shape of the user, identified by the muscle index and the fat index of the user, is formed by the effects of the user's lifestyle. Therefore, by calculating the ingredient amounts of the nutritional ingredients required for managing the body shape type in accordance with the selected body shape type of the user, it is possible to determine the nutritional ingredients and the ingredient amounts thereof suitable for the body shape of the user. Therefore, the nutritional ingredients considering the body shape formed by the effect of the user's lifestyle can be provided to the user.

Moreover, it is likely to assign different body shape types to multiple users because the body shape type of the user is determined based on two less correlated indexes. Therefore, it is possible to avoid a situation in which similar nutritional ingredients are provided to each the users.

According to the present embodiment, as the nutritional ingredients to be blended to the food, the fat accumulation inhibitory ingredient which inhibits the accumulation of fat and the vitality revitalizing ingredient which activates the vitality of the user are used. Examples of the fat accumulation inhibitory ingredient include the absorption inhibitory ingredient that inhibits the absorption of at least one of carbohydrate and lipid, and examples of the vitality revitalizing ingredient include at least one of the anti-fatigue ingredient of reducing fatigue and the anti-aging ingredient of maintaining youthfulness.

Then, among the nutritive ingredients described above, the nutritional ingredient determining unit 150 increases the fat accumulation inhibitory ingredient and decreases the vitality revitalizing ingredient as the fat index increases.

This provides the nutritional ingredients required for inhibiting fat gain to the user with more fat mass than a normal person. On the other hand, for a person with less fat mass generally tends to be tired or aged. For this reason, the nutritional ingredients such as the anti-fatigue ingredient and the anti-aging ingredient may be decreased for a user having a large amount of fat mass, and the nutritional ingredients such the anti-fatigue ingredient and the anti-aging ingredient may be reduced for a user having a small amount of fat mass.

According to the present embodiment, the muscle fitting ingredient which keeps muscle healthy and the muscle increasing ingredient which increases muscle are used as the nutritional ingredients to be blended to the food. Examples of the muscle fitting ingredient include a metabolism promoting ingredient that promotes muscle metabolism. Among the nutritional ingredients, the nutritional ingredient determining unit 150 increases the muscle fitting ingredient and decreases the muscle increasing ingredient as the muscle index increases.

This allows blending of appropriate nutritional ingredients for managing muscle, as the muscle fitting ingredient is increased while the muscle increasing ingredient that is less necessary is reduced for a user with more muscle mass than a normal person.

According to the present embodiment, the muscle mass of the user or the parameter correlated to the muscle mass is used as the muscle index, and the fat rate of the user is used as the fat index. The parameter correlated with the muscle mass is a calculation result calculated from the body composition data, and examples of the parameter include metabolism quantity, bone mass, or body water content.

As described above, by using the fat rate indicating the ratio of the fat mass in the body as the fat index, the magnitude relation of the fat mass to the size of the whole body such as the height or the weight of the user can be specified, so that nutritional ingredients required for user's body can be accurately determined. As the muscle index, the index calculated based on the muscle mass can be used instead of the muscle mass, and even if such an index is used, the body shape of the user can be classified finely like in the case using the muscle mass.

In the embodiment described above, the case in which the nutritional ingredients required for managing body shape of the user is determined was explained, but the nutritional ingredients required for realizing the change to the body shape which the user sets as the target (ideal) may be added.

Second Embodiment

Next, as the second embodiment of the present invention, a case in which supplemental nutritional ingredients which are nutritional ingredients supplementing the nutritional ingredients determined in the first embodiment are added to the supplement 21a in addition to the nutritional ingredients determined in the first embodiment will be described. In this case, as the supplemental nutritional ingredients, nutritional ingredients required for realizing the change of the user to the target body shape are blended to the supplement 21a.

Since the basic configuration of the ingredient determining apparatus of this embodiment is the same as that of the ingredient determining apparatus 30 of the first embodiment, the ingredient determining apparatus of this embodiment will be explained using the same reference numerals as the configuration of the ingredient determining apparatus 30 shown in FIG. 2.

Figure 6:
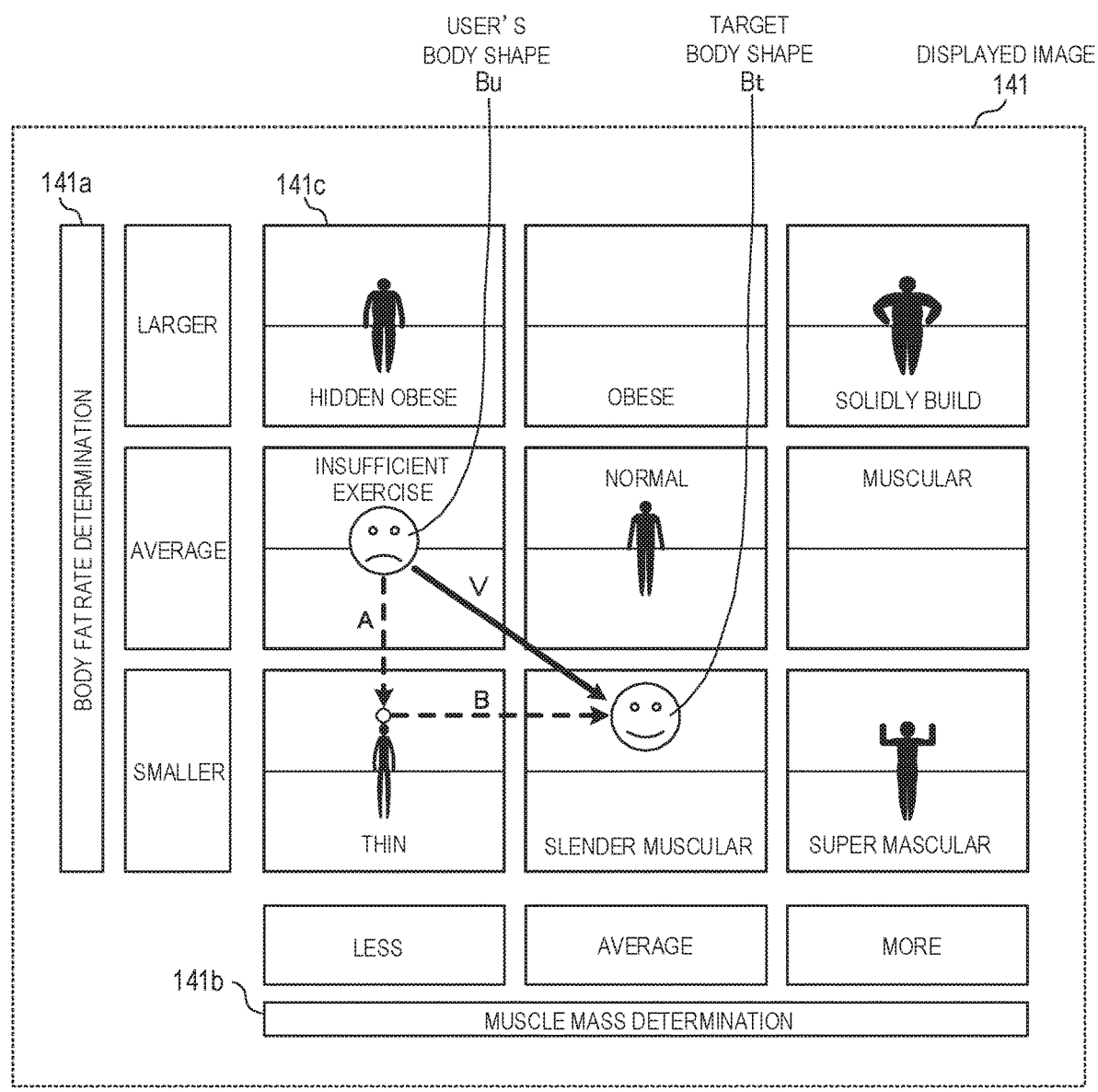
FIG. 6 is a diagram for explaining a method of calculating supplemental amounts of the nutritional ingredients based on a target body shape of the user in the second embodiment.

FIG. 6 is a diagram showing an example of a displayed image 141 displaying the body shape Bu and the target body shape Bt of the user. The body shape Bu of the user indicates the present body shape of the user selected by the body shape selecting unit 151 shown in FIG. 2.

The displayed image 141 includes a body fat rate determination area 141a indicating the determination result of the fat rate of the user, a muscle mass determination area 141b indicating the determination result of the muscle mass score of the user, and a body shape displaying area 141c displaying the body shape type of the user.

In the body fat rate determination area 141a, as the result of the fat rate determination, types of "larger", "average", and "smaller" are shown in a descending order of the fat rate setting the average value of the fat rate as the center value In the muscle mass determination area 141b, as the result of the muscle mass score determination, setting the average value of the muscle mass score as the center value, types of "less", "average" and "more" are shown in an ascending order of the muscle mass score.

In the body shape displaying area 141c, nine body shape types specified by the two indexes of the fat rate and the muscle mass score of the user are shown. In the body shapes where the muscle mass score belongs to the ranges of "less", the body shape types of "hidden obese", "insufficient exercise" and "thin" are assigned in a descending order of the fat rate.

In the body shapes where the muscle mass score belongs to the "average" range, the body shape types of "obese", "normal", and "slender muscular" are assigned in a descending order of the fat the rate. Further, in the body shapes where the muscle mass score belongs to the "more" range, the body shape types of "solidly built", "muscular" and "super muscular" are assigned in a descending order of the fat rate.

In this case, the body shape selecting unit 151 determines that the body shape Bu of the user belongs to the body shape type of "insufficient exercise." Then, the nutritional ingredient calculating unit 152 selects the types of the nutritional ingredients required for managing the health condition of the person whose body shape type corresponds to "insufficient exercise" and calculates the ingredient amounts of the nutritional ingredients.

In addition to the calculation processing of the nutritional ingredients and the ingredient amounts thereof described above, in the present embodiment, the calculation processing of the nutritional ingredients and the ingredient amount thereof required for realizing the change to the target body shape Bt targeted by the user is further executed. That is, in the present embodiment, the supplemental nutritional ingredients which supplement the nutritional ingredients required for managing the body shape of the user are determined.

Specifically, the target body shape Bt of the user is selected from among the body shape types shown in the body shape displaying area 141c and inputted to the operation unit 110 shown in FIG. 2. Thus, the operation unit 110 receives the target body shape information for identifying the target body shape Bt of the user. The display unit 140 displays the target body shape Bt of the user in the displayed image 141 as shown in FIG. 6 based on the received target body shape information.

In addition, the target body shape supplementation unit 153 obtains a target vector V indicating the divergence from the body shape Bu to the target body shape Bt of the user based on the target body shape data of the user, and decomposes the target vector V into a divergence A of the fat rate and a divergence B of the muscle mass score. The target body shape supplementation unit 153 then supplements the nutritional ingredients required for realizing the change to the target body shape Bt based on the magnitude and the orientation of both the divergence A of the fat rate and the divergence B of the muscle mass score.

The divergence A of the fat rate described above is a fat index component of the target vector V and indicates the divergence from the target of the fat rate required for realizing the change to the target body shape Bt. The divergence B of the muscle mass score is a muscle index component of the target vector V, and indicates the divergence from the target of the muscle mass score required for realizing the change to the target body shape Bt.

Next, the nutritional ingredients required for realizing the change to the target body shape Bt of the user and the method of calculating the supplemental amounts thereof will be described with reference to FIG. 7.

FIG. 7 is a diagram illustrating an example of a target body shape supplementation table 132 showing supplemental amounts Co1 and Co2 of the nutritional ingredients required for realizing the change to the target body shape Bt. The target body shape supplementation table 132 is stored in the body shape data holding unit 130 shown in FIG. 2, for example.

In the target body shape supplementation table 132, the supplemental amount Co1 of the nutritional ingredient which supplements the divergence A is associated with each of the divergences A of the fat index I1, and the supplemental amount Co2 of the nutritional ingredient which supplements the divergence B is associated with each of the divergences B of the muscle index I2.

In this case, the fat index I1 is the fat rate and the muscle index I2 is the muscle mass score. The supplemental amount Co1 of the nutritional ingredient with respect to the divergence A of the fat rate is the ingredient amount of the fat accumulation inhibitory ingredient, and the supplemental amount Co2 of the nutritional ingredient with respect to the divergence B of the muscle mass score includes the ingredient amount of the muscle increasing ingredient and the ingredient amount of the carbohydrate.

As for the divergence A and the divergence B, when the distance in the direction of the vertical axis and the distance in the direction of the horizontal axis shown in FIG. 6 are the same length, the absolute value of the divergence A and the absolute value of the divergence B are set to the same value. The absolute values of the divergences A and B increase in the order of Va1, Va2, Va3 and Va4.

As for the fat index I1, the fat accumulation inhibitory ingredient is supplemented depending on the divergence A of the fat rate. When the direction of the divergence A is the direction of increasing the fat rate (+ direction), the ingredient amount of the fat accumulation inhibitory ingredient is set to "0", and when it is the direction of decreasing the fat rate (−direction), the ingredient amount of the fat accumulation inhibitory ingredient is set to a value larger than "0".

When the direction of the divergence A is the direction of decreasing fat rate (− direction), the ingredient amount of the fat accumulation inhibitory ingredient increases as the absolute value of the divergence A increases. In this embodiment, a calculation formula for calculating the supplemental amount Co1 is set so that the coefficient to be multiplied by the basal metabolic rate BM [kcal/day] increases and the intercept increases as the divergence A approaches "−Va4" from "0".

On the other hand, for the muscle index I2, the muscle increasing ingredient to increase muscle and the carbohydrate to supply energy to the user are supplemented according to the divergence B of the muscle mass score.

In general, as the increase amount of muscle becomes large, more hard training is needed. Therefore, as a source of energy consumed in training, the carbohydrate is preferred over the protein which increases the muscle mass. However, since excessive ingestion of the carbohydrate promotes the accumulation of fat, the carbohydrate is set to have a smaller degree of increase in the amount of supplemental with respect to the increase in the divergence of the muscle index as compared with the muscle increasing ingredient.

As for the supplemental amount Co2 of the carbohydrate, as the divergence B of the muscle mass score becomes large, the ingredient amount of the carbohydrate increases. In this embodiment, a calculation formula for calculating the supplemental amount Co2 of the carbohydrate is set so that the coefficient to be multiplied by the basal metabolic rate BM increases and the intercept increases as the divergence B approaches "+Va4" from "0".

Further, as for the supplemental amount Co2 of the muscle increasing ingredient, when the direction of the divergence B is the direction of decreasing the muscle mass (− direction), the ingredient amount of the muscle increasing ingredient is set to "0". When the direction of the divergence B is the direction of increasing the muscle mass (+ direction), the ingredient amount of the muscle increasing ingredient is set to a value larger than "0".

When the direction of the divergence B is the direction of increasing the muscle mass (+ direction), the ingredient amount of the muscle increasing ingredient increases as the divergence B increases. In this embodiment, the calculation formula for calculating the supplemental amount Co2 of the muscle increasing ingredient is set so that the coefficient to be multiplied by the basal metabolic rate BM increases and the intercept increases as the divergence B approaches "+Va4".

Thus, the target body shape supplementation table 132 is set such as the absolute values of the divergences A and B, i.e., the distances in the directions of the vertical axis and the horizontal axis shown in FIG. 6, increase, the degrees of increase amounts of the supplemental amounts increase in the order of the fat accumulation inhibitory ingredient, the carbohydrate and the muscle increasing ingredient.

The reason why the degree of increase of the supplemental amount is increased as the absolute values of the divergences A and B are increased is that it is more difficult to increase the muscle mass than to decrease the fat mass. Specifically, a reduction in the fat mass can be achieved simply by preventing the ingredients responsible for the fat accumulation from being absorbed into the body. On the other hand, to increase the muscle mass, only absorbing ingredients that promote muscle reinforcement is not sufficient, and it is also required for causing a muscle development reaction by performing training or the like.

Using the target body shape supplementation table 132 set as described above, the target body shape supplementation unit 153 shown in FIG. 2 supplements the fat accumulation inhibitory ingredient if the divergence A of the fat index I1 is below a first threshold indicating "0". If the divergence A of the fat index I1 falls below the first threshold, it means that the divergence A decreases. In this case, the target body shape supplementation unit 153 increases the supplemental amount Co1 of the fat accumulation inhibitory ingredient as the divergence A becomes smaller than the first threshold.

On the other hand, if the divergence A of the fat index I1 is equal to or greater than the first threshold, i.e., the divergence A increases, the target body shape supplementation unit 153 inhibits the supplement of the fat accumulation inhibitory ingredient.

In addition, the target body shape supplementation unit 153 supplements the muscle increasing ingredient and the carbohydrate if the divergence B of the muscle index I2 exceeds a second threshold indicating "0". If the divergence B of the muscle index I2 exceeds the second threshold, it means that the divergence B increases. In this case, the target body shape supplementation unit 153 increases the supplemental amount Co2 of the muscle increasing ingredient and the carbohydrate as the divergence B becomes larger than the second threshold.

On the other hand, if the divergence B of the muscle index I2 is less than or equal to the second threshold, i.e., the divergence B decreases, the target body shape supplementation unit 153 inhibits the supplement of both the muscle increasing ingredient and the carbohydrate.

In this manner, the target body shape supplementation unit 153 calculates the supplemental amounts Co1 and Co2 of the nutritional ingredients associated with the target body shape supplementation table 132 based on the divergence A of the fat index I1 and the divergence B of the muscle index I2. This makes it possible to supplement the nutritional ingredients required for realizing the change to the target body shape Bt specified by the divergence A of the fat index I1 and the divergence B of the muscle index I2.

In this embodiment, the first and second thresholds are set to "0", but these thresholds may be values in the vicinity of "0", and these thresholds may be values different from each other. By adjusting the first and second thresholds in this manner, if there is a range in which the necessity of reducing the fat mass is low, it is possible to inhibit the supplement of the fat accumulation inhibitory ingredient in that range, and if there is a range in which the necessity of reducing the muscle mass is low, it is possible to inhibit the supplement of the muscle increasing ingredient and the carbohydrate in the same manner.

The calculation formula for calculating the supplemental amount Co1 for each range of the divergence A and the calculation formula for calculating the supplemental amount Co2 of the muscle increasing ingredient and the carbohydrate for each range of the divergence B are exemplary and not restrictive. However, when the divergence A becomes equal to or more than the first threshold value, and when the divergence B becomes equal to or less than the second threshold value, it is preferable that the degree of increase in the amount of supplement, which increases as the degree of the divergence increases, increases in the order of the fat accumulation inhibitory ingredient, the carbohydrate, and the muscle increasing ingredient.

The effect of fat reduction is more likely to appear than that of muscle increase, and the effect is more likely to appear visibly. For this reason, the supplemental amount Co1 may be increased at the beginning of the duration of continuous ingestion of the supplement 21a so as to prioritize the fat reduction compared with the muscle increase. This helps the user maintain a higher motivation at the beginning of the supplement 21a ingestion.

Next, a technique for encouraging nutritional ingredient ingestion by the user who ingests the above-mentioned nutritional ingredients toward realizing the target body shape is shown. A brief description will be given with reference to FIG. 8.

Figure 8:
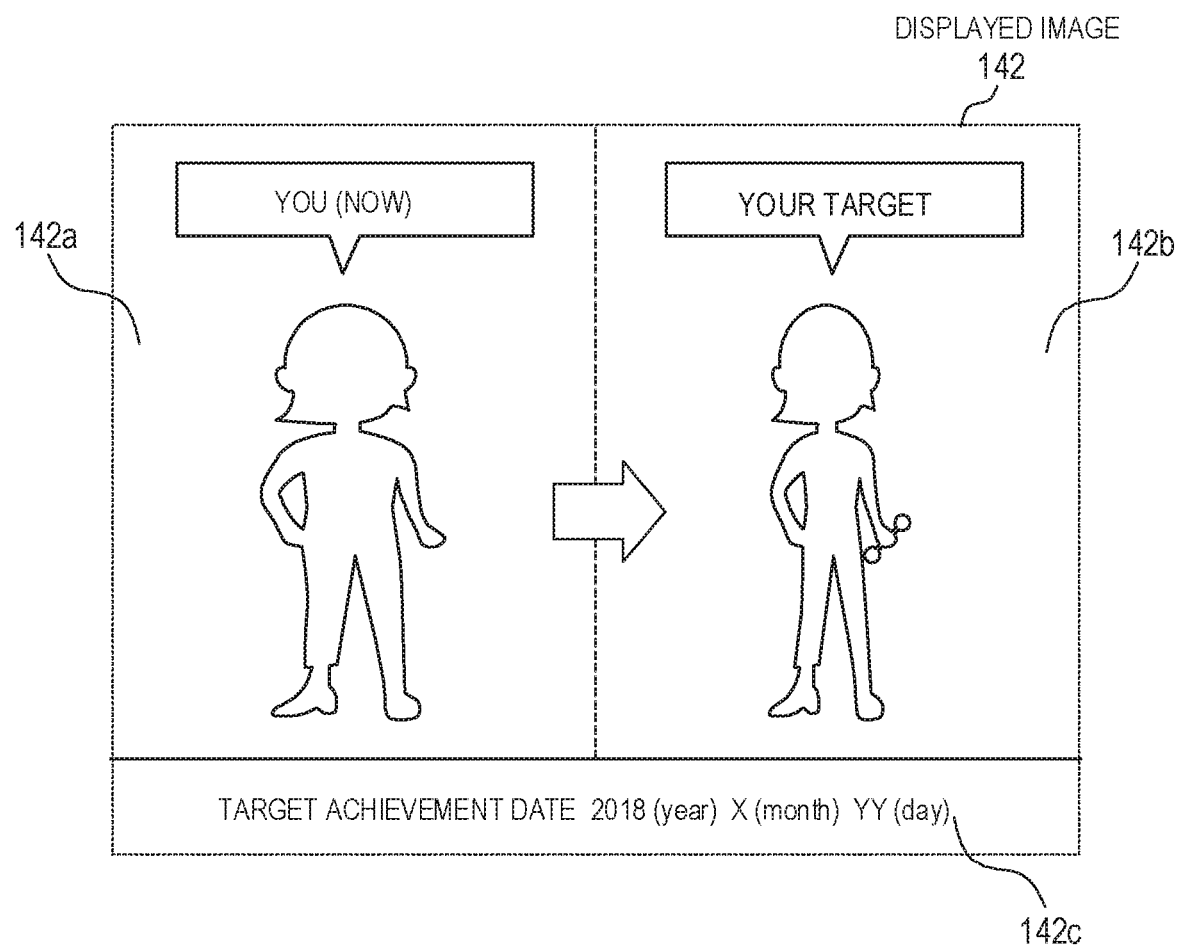
FIG. 8 is a diagram showing an example of a displayed image showing an external appearance of the user who achieved the target body shape.

FIG. 8 is a diagram illustrating an example of a displayed image 142 in which the outline of the user is abstractly displayed when the target body shape Bt is realized. The displayed image 142 is displayed by, for example, the display unit 140.

The displayed image 142 includes a region 142a for displaying the outline of the body shape Bu of the user, a region 142b for displaying the outline of the target body shape Bt, and a region 142c for displaying the target achievement date when the body shape Bu of the user reaches the target body shape Bt.

Thus, by displaying the outline of the person who achieved the target body shape Bt to the user, it is expected that the user will become willing to improve the body shape and will continue to ingest the supplement 21a generated by the generating apparatus 20.

If the user measures their body composition regularly and the ingredient determining apparatus 30 can obtain the body composition information of the user regularly, the previously selected target body shape Bt may be maintained without re-selecting it. As a result, since the nutritional ingredients are determined using the divergence from the body shape Bu to the target body shape Bt of the user at the time when user selected the target body shape Bt, it is possible to determine the nutritional ingredients according to the degree of achievement of the target.

The ingredient determining apparatus 30 may obtain the duration from when the previous value is obtained to when the current value is obtained and the change of body composition in this duration based on the body composition information, judge the effect of the supplement 21a using these, and correct the supplemental amounts according to the effect. Thus, when the supplement 21a is too effective, the ingredient amount of supplement 21a can be reduced, while when the effect of the supplement 21a is poor, the ingredient amount of the supplement 21a can be increased. For this reason, by the target body shape date shown in FIG. 8, the body shape of the user can be brought close to the target body shape Bt.

In addition, the ingredient determining apparatus 30 may evaluate the effectiveness of supplement 21a for each of the fat index and the muscle index using the duration and the change in the body composition of the user described above, and correct the supplemental amounts for the fat index and the muscle index, respectively, according to the evaluated value.

For example, the ingredient determining apparatus 30 may reduce the supplemental amount for the index if evaluated value of the effect of the supplement 21a is larger than the threshold, i.e., the supplement 21a is effective. On the other hand, when the evaluated value of the effect of the supplement 21a is smaller than the threshold, i.e., the supplement 21a is not effective, the supplemental amount for the index is increased. Thus, it is possible to determine the nutritional ingredients in view of the ease of appearance of the effect of the respective ingredients caused by the individual difference such as the constitution of the user In the present embodiment, the supplemental amounts Co1 and Co2 of the nutritional ingredients required for realizing the change to the target body shape Bt are calculated based on the present muscle mass and fat mass of the user, but the present invention is not limited thereto. For example, the tendency of the muscle mass of the user to increase and decrease, and the tendency of the body fat rate to increase and decrease may be specified, and the supplemental amounts Co1 and Co2 of the nutritional ingredients may be weighted according to the specified tendency.

In the present embodiment, an example in which the user enters the body shape type as the target body shape information into the operation unit 110 has been described, but the input of the target body shape information is not limited to this. For example, as the target body shape information, an increase amount or a decrease amount of each index may be inputted for both the fat index and the muscle index with respect to the present body shape Bu of the user. Alternatively, the fat index and the muscle index values may be entered directly as the target body shape information, and at least the target body shape Bt orientation and the degree of the orientation from the body shape Bu to the target body shape Bt of the user may be entered.

Next, the operation and effect of the second embodiment will be described.

According to the second embodiment, the ingredient determining apparatus 30 further includes the operation unit 110 as a receiving means for receiving the target body shape information indicating the target body shape Bt targeted by the user. The nutritional ingredient determining unit 150 further includes the target body shape supplementation unit 153 as a supplementing means for determining supplemental nutrition ingredients for supplementing the nutritional ingredients required for managing the body shape Bu of the user based on the target vector V indicating the divergence from the body shape Bu to the target body shape Bt of the user. The supplemental nutritional ingredients may include the nutritional ingredients required for realizing the change to the target body shape Bt.

This makes it possible to blend not only the nutritional ingredients required for managing the body shape Bu specified by the fat index and the muscle index of the user but also the nutritional ingredients required for realizing the change to the target body shape Bt. For this reason, highly effective nutritional ingredients can be accurately provided in order to realize the body shape idealized by the user in accordance with the health condition in the user's body. Furthermore, the ingredient determining apparatus 30 may determine the ingredient amounts of the supplemental nutritional ingredients based on the target vector V and this realizes a finer blending.

According to this embodiment, as shown in FIG. 7, the target body shape supplementation unit 153 determines whether the divergence A, which is the fat index component of the target vector V, falls below the first threshold, i.e., is decreasing. The target body shape supplementation unit 153 then supplements the fat accumulation inhibitory ingredient which inhibits the accumulation of fat when the divergence A of the fat index is below the first threshold. The first threshold referred to herein is defined to prevent the user from being hindered from realizing the change to the target body shape Bt by ingesting the fat accumulation inhibitory ingredient. The first threshold is set to, for example, "0".

The target body shape supplementation unit 153 may determine whether the fat mass of the user needs to be reduced based on the target body shape Bt of the user like this, and may provide the fat accumulation inhibitory ingredient to the user if it determines that fat mass needs to be reduced. This allows the body shape Bu of the user to approach the target body shape Bt, taking the status in the body of the user into account.

According to this embodiment, as shown in FIG. 7, the target body shape supplementation unit 153 supplements the muscle increasing ingredient which increases the muscle, if the divergence B, which is the muscle index component of the target vector V, exceeds the second threshold, i.e. is increasing. The second threshold is defined to prevent the user from being hindered from realizing the change to the target body shape Bt by ingesting the muscle increasing ingredient. The second threshold value is set to, for example, "0".

In this way, the target body shape supplementation unit 153 determines whether or not the muscle mass of the user needs to be increased based on the target body shape Bt of the user, and when it determines that the muscle mass needs to be increased, it can provide the muscle increasing ingredient to the user. This allows the body shape Bu of the user to approach the target body shape Bt, taking the status in the body of the user into account.

According to this embodiment, the carbohydrate is used as the nutritional ingredient to be blended into the supplement 21a. The target body shape supplementation unit 153 then increases the supplemental quantity of the carbohydrate as the divergence B of the muscle index increases. This makes it easier to increase the muscle mass of the user compared to simply providing the protein to increase the muscle mass, since in addition to the muscle increasing ingredient, the user is provided with the carbohydrate to replenish the energy consumed in the workout.

Third Embodiment

Next, as the third embodiment of present invention, an example in which nutritional ingredients for avoiding lifestyle diseases are added to the nutritional ingredients determined in the first embodiment will be described below. The basic configuration of the ingredient determining apparatus of the present embodiment is the same as that of the ingredient determining apparatus 30 of the first embodiment.

FIG. 9 is a diagram illustrating an example of a lifestyle disease prevention table 133 defined to reduce the risk of lifestyle diseases. The lifestyle disease prevention table 133 is stored in, for example, the body shape data holding unit 130.

In the lifestyle disease prevention table 133, the types of the nutritional ingredients and ingredient amount thereof required for the lifestyle disease prevention are associated with each of the biometric indexes that specify the risk of lifestyle diseases. In the present embodiment, the four biometric index determination tables T1 to T4 are set.

In the determination table T1, a basal metabolic rate W is associated as one of the biometric indexes for specifying the risk of lifestyle diseases. The basal metabolic rate W is calculated based on the muscle mass, age, sex, and the like of the user. As the basal metabolic rate W decreases, the risk of metabolism abnormality and the like becomes high.

Further, in the determination table T1, the metabolism activating ingredient and the blood circulation promoting ingredient are associated as the nutritional ingredients required for improving the basal metabolic rate W. The metabolism activating ingredient is a nutritional ingredient which activates the basal metabolism, and mainly includes arginine and the like. The blood circulation promoting ingredient is a nutritional ingredient that promotes blood circulation, and includes, for example, arginine, maca, or the like.

For each ingredient amount of the metabolism activating ingredient and the blood circulation promoting ingredient, the standard range of basal metabolic rate W is associated with a medium addition amount A2, and the high range and the low range relative to the standard range are associated with a small addition amount A1 and a large addition amount A3, respectively. The addition amounts A1 to A3 are predetermined values.

In the present embodiment, the nutritional ingredient determining unit 150 refers to the determination table T1, and when the basal metabolic rate W is lower than the standard range, selects the metabolism activating ingredient and the blood circulation promoting ingredient as the nutritional ingredients for reducing the risk of lifestyle diseases, and increases the respective amounts thereof. As a result, the basal metabolic rate W of the user tends to increase, so it is possible to prevent the risk of lifestyle diseases such as the metabolism abnormality caused by the decreased basal metabolic rate W.

In the determination table T2, a visceral fat mass X is associated as one of the biometric indexes for specifying the risk of lifestyle diseases. As the visceral fat mass X increases, the risk of the metabolic syndrome, etc becomes high.

Further, in the determination table T2, an antioxidant ingredient, a lipolytic ingredient, and a lipid metabolism promoting ingredient are associated as nutritional ingredients required for improving the visceral fat mass X. The antioxidant ingredient is a nutritional ingredient required for inhibiting oxidation, and mainly includes polyphenol and the like. The lipolytic ingredient is a nutritional ingredient required for decomposing fat, and includes dietary fiber and the like, for example. The lipid metabolism promoting ingredient is a nutritional ingredient which promotes the metabolism of lipids, and includes dietary fiber, lecithin and the like, for example.

For each ingredient amount of the three nutritional ingredients, the standard range of the visceral fat mass X is associated with a medium addition amount B2, and a small range and a large range relative to the standard range are associated with a small addition amount B1 and a large addition amount B3, respectively. The addition amounts B1 to B3 are predetermined values.

In the present embodiment, the nutritional ingredient determining unit 150 refers to the determination table T2, and when the visceral fat mass X exceeds the standard range, selects the antioxidant ingredient, the lipolytic ingredient, and the lipid metabolism promoting ingredient as the nutritional ingredients for reducing the risk of lifestyle diseases, and increases the respective amounts thereof. This allows the visceral fat mass X of the user to be reduced easily, thereby preventing the risk of lifestyle diseases such as arteriosclerosis caused by the increased visceral fat mass X.

In the determination table T3, a bone mass Y is associated as one of the biometric indexes for specifying the risk of lifestyle diseases. As the bone mass Y decreases, the risk of osteoporosis, etc. becomes high.

Further, in the determination table T3, a bone forming ingredient and a bone metabolism supplemental ingredient are associated as nutritional ingredients required for improving the bone mass Y. The bone forming ingredient is a nutritional ingredient required for forming bone, and mainly includes calcium and the like. The bone metabolism supplemental ingredient is a nutritional ingredient which assists in the metabolism of bone, and includes magnesium and vitamin D, for example.

For each ingredient amount of the two nutritional ingredients, the standard range of the bone mass Y is associated with a medium addition amount C2, and a large range and a small range relative to the standard range are associated with a small addition amount C1 and a large addition amount C3, respectively. The addition amounts C1 to C3 are predetermined values.

In the present embodiment, the nutritional ingredient determining unit 150 refers to the determination table T3, and when the bone mass Y is lower than the standard range, selects the bone forming ingredient and the bone metabolism supplemental ingredient as the nutritional ingredients for reducing the risk of lifestyle diseases, and increases the respective amounts thereof. This allows the bone mass Y of the user to increase easily, thereby preventing the risk of lifestyle diseases such as osteoporosis caused by the reduced bone mass Y.

In the determination table T4, a body water balance Z is associated as one of the biometric indexes for specifying the risk of lifestyle diseases. The body water balance Z is a value obtained by evaluating the balance between the intracellular fluid and the extracellular fluid. As the body water balance Z deteriorates, the risk of the hypertension, etc. becomes high.

Further, in the determination table T4, an excretion promoting ingredient and a blood flow smoothing ingredient are associated as nutritional ingredients required for improving the body water balance Z. The excretion promoting ingredient is a nutritional ingredient that promotes the discharge of excessive body water or salinity, and includes mainly potassium and the like. The blood flow smoothing ingredient is a nutritional ingredient required for inhibiting the stagnation of the blood flow or the lymphatic fluid flow, and includes melilot and the like, for example.

Then, for each ingredient amount of the two nutritional ingredients, the standard range of the body water balance Z is associated with a medium addition amount D2, and a better range and a worse range relative to the standard range are associated with a small addition amount D1 and a large addition amount D3, respectively. The addition amounts D1 to D3 are predetermined values.

In the present embodiment, the nutritional ingredient determining unit 150 refers to the determination table T4, and when the body water balance Z falls below the standard range, selects the excretion promoting ingredient and the blood flow smoothing ingredient as the nutritional ingredients for reducing the risk of lifestyle diseases, and increases the respective amounts thereof. As a result, the body water balance Z of the user approaches a good condition, and therefore, it is possible to prevent the risk of lifestyle diseases such as hypertension caused by the deteriorated body water balance Z.

By using this lifestyle disease prevention table 133, the nutritional ingredient determining unit 150 can determine the amounts of the improvement ingredients to be added based on at least one biometric index of the basal metabolic rate W, the visceral fat mass X, the bone mass Y and the body water balance Z. Examples of the improvement ingredients include the metabolism activating ingredient, the blood circulation promoting ingredient, the antioxidant ingredient, the lipolytic ingredient, the lipid metabolism promoting ingredient, the bone forming ingredient, the bone metabolism supplemental ingredient, the excretion promoting ingredient and the blood flow smoothing ingredient as described above.

In this manner, based on the biometric index identifying the risk of the predetermined lifestyle diseases, the nutritional ingredient determining unit 150 of the present embodiment determines the improvement ingredients for that biometric index.

Next, a method of providing the supplement 21a in which the ingredient amounts of the nutritional ingredients determined in the respective embodiments are blended will be described briefly with reference with reference to FIG. 10.

Figure 10:
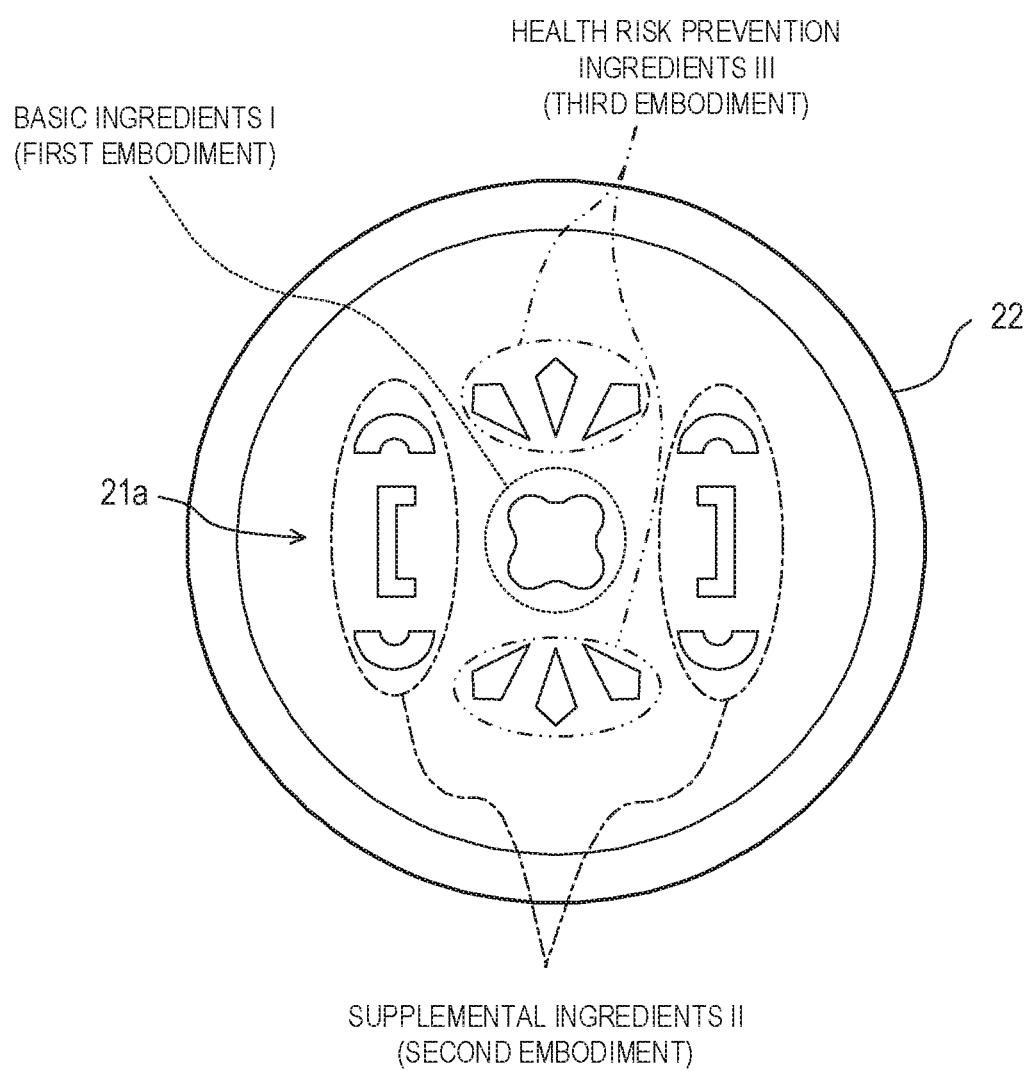
FIG. 10 is a conceptual diagram illustrating an example of a providing form of a supplement to the user.

FIG. 10 is a diagram illustrating an example of the supplement 21a on the dish 22 disposed by the generating apparatus 20;

As shown in FIG. 10, the supplement 21a provided by the generating apparatus 20 to the dish 22 is composed of basic ingredients I shown by a dashed line, supplemental ingredients II shown by a dashed line, and a health risk prevention ingredients III shown by a double-dashed line.

The basic ingredients I are supplements (supplementary foods) including the nutritional ingredients determined in the first embodiment. As shown in FIG. 4, the nutritional ingredients required for managing the body shape Bu of the user are included.

Also in the present embodiment, the nutritional ingredient determining unit 150 selects the nutritional ingredients required for managing the body shape of the user from among the fat accumulation inhibitory ingredient, the vitality revitalizing ingredient, the muscle increasing ingredient, the muscle fitting ingredient based on the fat index and the muscle index of the user, and determines the ingredient amounts of the nutritional ingredients.

The supplemental ingredients II are supplements including the nutritional ingredients determined in the second embodiment, and as shown in FIG. 7, the nutritional ingredients required for realizing the change of the user to the target body shape Bt are included.

Also in the present embodiment, the nutritional ingredient determining unit 150 selects the nutritional ingredients required for realizing the change to the target body shape Bt from among the fat accumulation inhibitory ingredient, the muscle increasing ingredient and the carbohydrate based on the divergence A of the fat index and the divergence B of the muscle index of the user, and supplement the ingredient amounts of the nutritional ingredients.

The health risk prevention ingredients III are supplements including the nutritional ingredients determined in the third embodiment, and as shown in FIG. 9, the nutritional ingredients required for preventing lifestyle diseases of the user are included.

In the present embodiment, the basal metabolic rate W, the visceral fat mass X, the bone mass Y and the body water balance Z are used as the biometric indexes for specifying the risk of lifestyle diseases. Based on these biometric indexes, the nutritional ingredients required for improving the biometric indexes of the user are selected from among the metabolism activating ingredient, the blood circulation promoting ingredient, the antioxidant ingredient, the lipolytic ingredient, the lipid metabolism promoting ingredient, the bone forming ingredient and the bone metabolism supplemental ingredient, and the ingredient amounts of the nutritional ingredients are determined.

Thus, the food including the basic ingredients I necessary for managing the body shape Bu of the user, the supplemental ingredients II necessary for realizing the change of the user to the target body shape Bt, and the health risk prevention ingredients III necessary for preventing lifestyle diseases of the user is provided from the generating apparatus 20 to the user.

Next, the operation of the ingredient determining apparatus 30 in the present embodiment will be described with reference to FIGS. 11 and 12. The ingredient determining apparatus 30 may include only the first embodiment, or may include only at least one of the second embodiment and the third embodiment. FIG. 12 shows an example of the operation of the ingredient determining apparatus 30 including all embodiments is shown.

Figure 11:
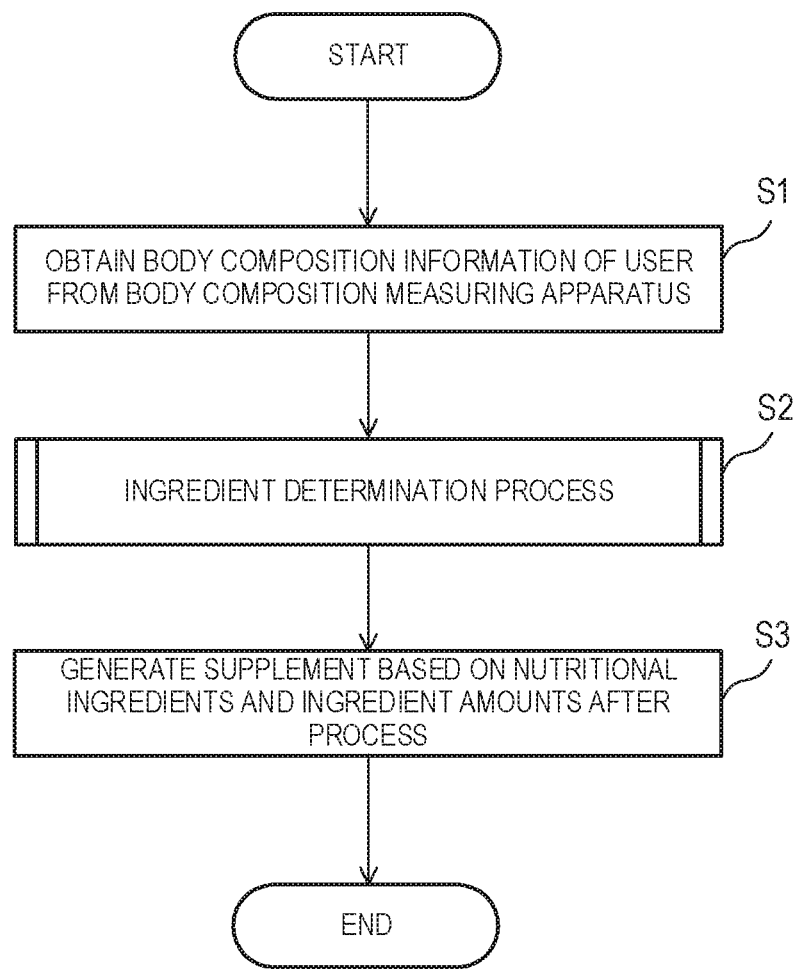
FIG. 11 is a flow chart showing an example of a method of determining the nutritional ingredients according to the present embodiment.
Figure 12:
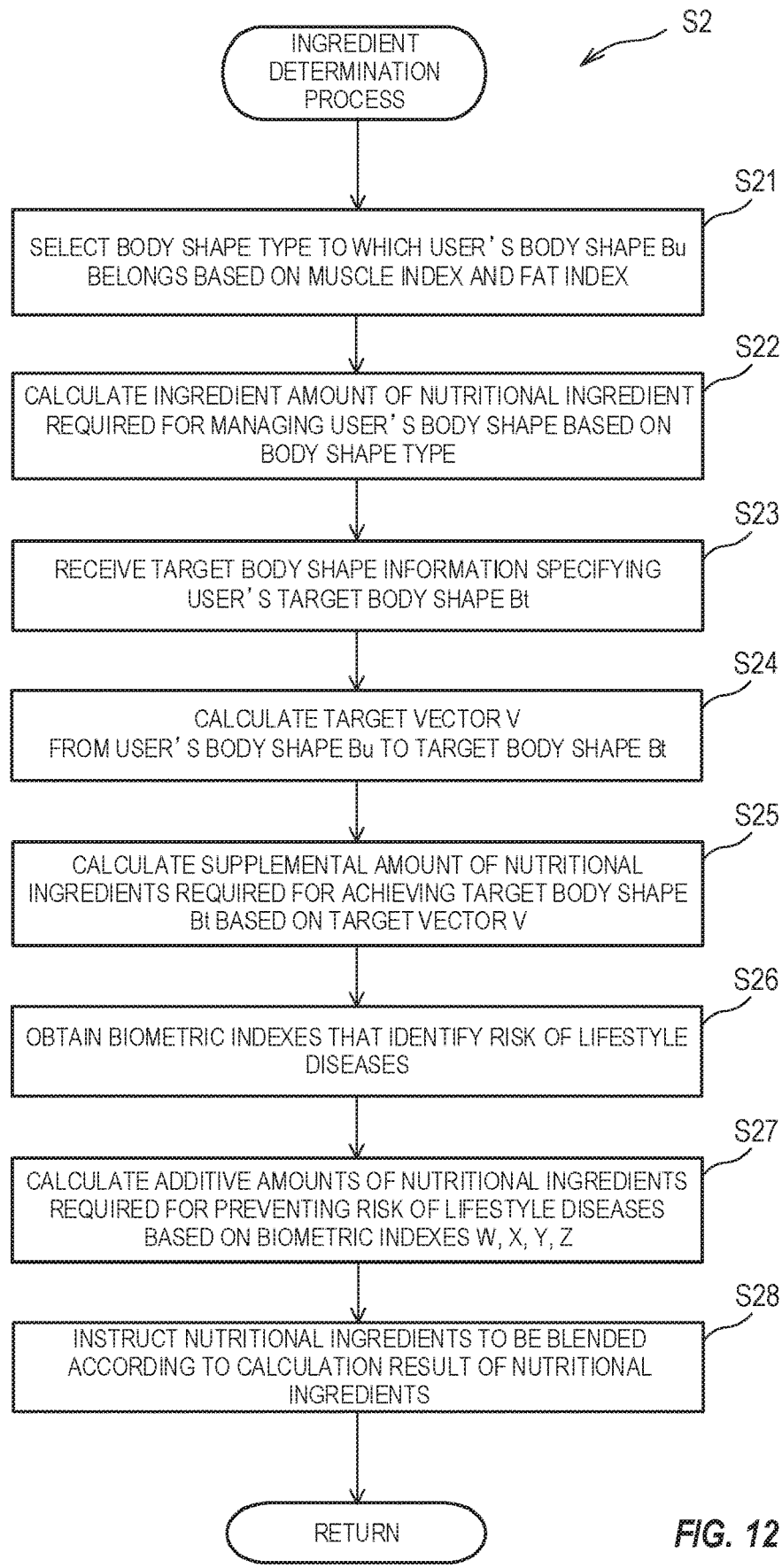
FIG. 12 is a flowchart showing an example of an ingredient determining process included in the method shown in FIG. 11.

FIG. 11 is a flow chart showing an example of the process for determining the nutritional ingredients according to the present embodiment.

In step S1, the body composition information obtaining unit 120 obtains the body composition information including the fat index and the muscle index of the user from the communication device 8 of the body composition measuring apparatus 10.

In step S2, the nutritional ingredient determining unit 150 executes the ingredient determination process for determining the nutritional ingredients of the supplement 21a based on the obtained fat index and muscle index of the user. The details of this ingredient determination process will be described later with reference to FIG. 12. The nutritional ingredient instruction unit 160 instructs the ingredient amounts of the nutritional ingredients determined by the nutritional ingredient determining unit 150 to the generating apparatus 20.

In step S3, the generating apparatus 20 provides the supplement 21a on the dish 22 based on the ingredient amounts of the nutritional ingredients instructed by the nutritional ingredient instruction unit 160. Specifically, the generating apparatus 20 selects containers containing supplement materials including the instructed nutritional ingredients from among a plurality of containers 21 based on the instructed nutritional ingredients. The generating apparatus 20 then generates the supplement 21a by extracting a predetermined number of supplement materials from each of the selected containers based on the ingredient amounts of the instructed nutritional ingredients and provides the generated supplement 21a.

When the process of step S3 ends, the control unit 180 ends a series of procedures of the nutritional ingredient determining method.

FIG. 12 is a flowchart showing an example of the procedures of the ingredient determining process executed in step S2.

In step S21, the body shape selecting unit 151 determines the body shape Bu of the user based on the muscle index and the fat index of the user obtained by the body composition information obtaining unit 120. In this embodiment, as shown in FIG. 3, the body shape selecting unit 151 selects the body shape type to which the body shape Bu of the user belongs from among the nine body shape types based on the fat rate and the muscle mass score of the user.

In step S22, the nutritional ingredient calculating unit 152 calculates the ingredient amounts of the basic ingredients I, which are the nutritional ingredients required for managing the body shape Bu of the user, based on the body shape type to which body shape Bu of the user belongs. In this embodiment, the nutritional ingredient calculating unit 152 refers the body shape management table 131 shown in FIG. 5, specifies the ratio of the basic ingredients I associated with the body shape type to which body shape Bu of the user belongs, and calculates the ingredient amounts of the basic ingredients I based on the ratio.

In step S23, the operation unit 110 receives the target body shape specifying the target body shape Bt of the user through the user's input operation.

In step S24, the target body shape supplementation unit 153 calculates the target vector V indicating the divergence from the body shape Bu to the target body shape Bt of the user based on the target body shape information.

In step S25, the target body shape supplementation unit 153 calculates the supplemental amounts of the supplemental ingredients II, which are the nutritional ingredients required for realizing the change to the target body shape Bt, based on the target vector V of the user.

In this embodiment, the target body shape supplementation unit 153 decomposes the target vector V of the user into the divergence A of the fat rate and the divergence B of the muscle mass score. The target body shape supplementation unit 153 refers the target body shape supplementation table 132 shown in FIG. 7, calculates the supplemental amount Co1 of the supplemental ingredients II associated with the divergence A of the decomposed fat rate, and calculates the supplemental amount Co2 of the supplemental ingredients II associated with the divergence B of the decomposed muscle mass score.

In step S26, the body composition information obtaining unit 120 obtains the biometric indexes that identify the risk of lifestyle diseases of the user. In this embodiment, as shown in FIG. 9, the body composition information obtaining unit 120 obtains at least one biometric index of the basal metabolic rate W, the visceral fat mass X, the bone mass Y and the body water balance Z of the user In step S27, the nutritional ingredient determining unit 150 calculates the additive amounts of the health risk prevention ingredients III, which are the nutritional ingredients required for reducing the risk of lifestyle diseases, based on the biometric indexes from the body composition information obtaining unit 120.

In this embodiment, as shown in FIG. 9, when the nutritional ingredient determining unit 150 determines that the basal metabolic rate W is low, the metabolism activating ingredient and the blood circulation promoting ingredient are selected as the health risk prevention ingredients III, and the additive amount of each ingredient is increased. When the nutritional ingredient determining unit 150 determines that the visceral fat mass X is large, the antioxidant ingredient, the lipolytic ingredient and the lipid metabolism promoting ingredient are selected as the health risk prevention ingredients III, and the additive amount of each ingredient is increased. Further, when the nutritional ingredient determining unit 150 determines that the bone mass Y is small, the bone forming ingredient and the bone metabolism supplemental ingredient are selected as the health risk prevention ingredients III, and the additive amount of each ingredient is increased. Then, when the nutritional ingredient determining unit 150 determines that the body water balance Z is bad, the excretion promoting ingredient and the blood flow smoothing ingredient are selected as the health risk prevention ingredients III, and the amount of each ingredient is increased.

In step S28, the nutritional ingredient determining unit 150 outputs the calculation result of the above-described nutritional ingredients to the nutritional ingredient instruction unit 160 as the ingredient determining information.

Specifically, the nutritional ingredient determining unit 150 generates and outputs the ingredient determining information indicating ingredient amounts of the basic ingredients I calculated in step S22, the supplemental amounts of the supplemental ingredients II calculated in step S25, and the additive amounts of the health risk prevention ingredients III calculated in step S27. Based on the ingredient determining information, the nutritional ingredient instruction unit 160 instructs blending of the ingredient amounts of the basic ingredients I, the supplemental amounts of the supplemental ingredients II and the additive amounts of the health risk prevention ingredients III.

When the process in step S28 is completed, the control unit 180 terminates the subroutine of the ingredient determination process, and then returns to the nutritional ingredient determining method shown in FIG. 11. The processing of steps S23 to S27 may be omitted, or the processing of any one of steps S23 to S25 and steps S26 and S27 may be omitted.

In the present embodiment, the health risk prevention ingredients III are determined by using the biometric indexes specifying the risk of lifestyle diseases, but the nutritional ingredient determining unit 150 may determine the adjustment ingredients IV as another nutritional ingredients for adjusting the condition of the body by using the measurement result of another measuring device.

For example, as another measuring device, an exhalation measuring device may be used in which acetone in exhalation of the user is measured to calculate the lipid metabolism evaluation value based on the measurement value. In this case, the body composition information obtaining unit 120 receives the lipid metabolism evaluation value of the user from the exhalation measuring device, and the nutritional ingredient determining unit 150 calculates the additive amounts of at least one of the adjustment ingredients IV, e.g., the antioxidant ingredient, the lipolytic ingredient, the lipid metabolism promoting ingredient and the like, based on the lipid metabolism evaluation value.

Alternatively, as another measuring device, a physical activity measuring device which measures physical activity of the user and calculates an activity evaluation value which evaluates the measured physical activity of the previous day, the last week and the like of the measurement date. In this case, the body composition information obtaining unit 120 receives an activity evaluation value of the user from the physical activity measuring device, and the nutritional ingredient determining unit 150 calculates the additive amounts of at least one of the adjustment ingredients IV, e.g., the metabolism activating ingredient, the blood circulation promoting ingredient and the like, based on the activity evaluation value.

Alternatively, as another measuring device, a sleep measuring device which measures the sleep condition of the user and calculates a sleep evaluation value which evaluates the quality of sleep based on the measurement value, may be used. In this case, the body composition information obtaining unit 120 receives the sleep evaluation value of the user from the sleep measuring device, and the nutritional ingredient determining unit 150 calculates the additive amounts of the adjustment ingredients IV, e.g., the anti-fatigue ingredient and the like, based on the sleep evaluation value.

As another embodiment, the nutritional ingredient determining unit 150 of any one of the first embodiment to the third embodiment may further determine the adjustment ingredients IV and the ingredient amounts thereof using the measurement results of another measuring device as described above. That is, the nutritional ingredient determining unit 150 determines the ingredient amounts of the adjustment ingredients IV in addition to at least one of the ingredient amounts of the basic ingredients I, the supplemental amounts of the supplemental ingredients II, and the additive amounts of the health risk prevention ingredients III.

In the embodiment described above, the body composition information obtaining unit 120 determines the nutritional ingredients and the ingredient amounts thereof based on the body composition data, but the present invention is not limited to this. For example, the body composition information obtaining unit 120 may estimate the nutritional ingredients and the ingredient amounts thereof to be ingested by meals, and subtract the estimated nutritional ingredient and ingredient amounts from the ingredient amounts of the nutritional ingredients determined in the embodiments described above. In this case, the nutritional ingredient determining unit 150 determines the nutritional ingredients and ingredient amounts thereof of the supplement 21a by subtracting the estimated ingredient amounts of the nutritional ingredients expected to be ingested in the diet from the ingredient amounts of the determined nutritional ingredients.

The nutritional ingredients and the ingredient amounts expected to be ingested in the diet may be constant or may be estimated by answering questions about the diet or may be estimated by obtaining or analyzing other data from a diet management application, or the like.

Next, the operation and effect of the third embodiment will be described.

According to the third embodiment, based on the values of the biometric indexes that identify the risk of the predetermined lifestyle diseases, the nutritional ingredient determining unit 150 determines the additive amounts of the improvement ingredients required for improving the biometric indexes. As described above, since the additive amounts of the improvement ingredients are determined according to the degree of the risk of lifestyle diseases, it is possible to reduce the risk of lifestyle diseases of the user. The nutritional ingredient determining unit 150 may determine the types of the improvement ingredients only and even in this case, the risk of lifestyle diseases of the user can be reduced.

According to this embodiment, as shown in FIG. 9, at least one of the basal metabolic rate W, the visceral fat mass X, the bone mass Y and the body water balance Z in the body of the user is used as the biometric indexes which identify the risk of lifestyle diseases.

As the improvement ingredient for the basal metabolic rate W, at least one nutritional ingredient of the metabolism activating ingredient in which the basal metabolism is activated and the blood circulation promoting ingredient in which the blood circulation is promoted is used. As the improvement ingredient for the visceral fat mass X, at least one nutritional ingredient of the antioxidant ingredient, the lipolytic ingredient which decomposes fat, and the lipid metabolism promoting ingredient which promotes the metabolism of lipid is used. As the ingredient for the bone mass Y, at least one nutritional ingredient of the bone forming ingredient which forms bone and the bone metabolism supplemental ingredient which assists metabolism of bone is used.

As described above, since the metabolism activating ingredient and the blood circulation promoting ingredient are increased in accordance with the decrease in the basal metabolic rate W of the user, it is possible to prevent user from causing the metabolic disorder. Since the amounts of the antioxidant ingredient, the lipolytic ingredient and lipid metabolism promoting ingredient are increased as the visceral fat mass X of the user is increased, it is possible to reduce the risk of the user becoming the metabolic syndrome. That is, it is possible to reduce the health risk of dyslipidemia, high blood pressure, fasting hyperglycemia, and the like. Furthermore, since the amounts of the bone forming ingredient and the bone adjustment ingredient are increased as the bone mass Y of the user decreases, it is possible to prevent the risk of the osteoporosis.

Although the embodiments of the present invention have been described in the above, the above-mentioned embodiments merely illustrate a part of application examples of the present invention, and the technical scope of the present invention is not intended to be limited to the specific configurations in the above-mentioned embodiments.

In the above-described embodiment, as the embodiment of the ingredient determining apparatus 30 for determining the nutritional ingredients required for the user's body according to the health condition in the user's body, the mode for determining the types and the ingredient amounts of nutritional ingredients has been described, but only the types of nutritional ingredients may be determined.

In the above-described embodiment, an example has been described in which the generating apparatus 20 generates the supplement 21a by blending the supplement materials extracted from each of the containers 21 by an arbitrary amount, but the generating apparatus 20 is not limited thereto. For example, each of the plurality of containers 21 of the generating apparatus 20 contains supplement (supplementary food) in capsules, pills, tablets, or other shapes, and different types of supplements may be contained in each of the containers 21. In this case, the generating apparatus 20 may provide a combination of supplements by selecting predetermined containers from among a plurality of containers 21 depending on the ingredients and the ingredient amounts determined by the ingredient determining apparatus 30.

The generating apparatus 20 may execute a settlement process with money or electronic money when providing the supplement 21a, and provide the supplement 21a when the settlement is completed.

The present application claims a priority based on Japanese Patent Application No. 2018-066021 filed with the Japan Patent Office on Mar. 29, 2018, the entire contents of which are incorporated into this specification by reference.

DESCRIPTION OF THE REFERENCE NUMERALS 10 body composition measuring apparatus
20 generating apparatus
30 ingredient determining apparatus
110 operation unit (receiving means)
120 body composition information obtaining unit (obtaining means)
130 body shape data holding unit (holding means)
150 nutritional ingredient determining unit (determining means)

151 body shape selecting unit (selecting method)
152 nutritional ingredient calculating unit (calculating means)
153 target body shape supplementation unit (supplementing means)
170 storage unit (programs)

The invention claimed is:

1. An ingredient determining apparatus configured to determine nutritional ingredients in food provided for a user, comprising:
a receiver configured to receive body shape data indicating a target body shape targeted by the user; and
a processor configured to be attachable to and in electrical contact with a generating apparatus, the processor comprising:
a body composition information obtaining circuit configured to obtain a muscle index indicating a degree of muscle mass of the user and a fat index indicating a degree of fat mass of the user from data generated by a body composition measuring apparatus that is configured to measure impedance of at least one body part of the user from a voltage value detected by a voltage detecting circuit, and then calculate the muscle index and the fat index based on the measured impedance values,
a nutritional ingredient determining circuit that includes a nutritional ingredient calculating circuit that is configured to determine the nutritional ingredients based on the muscle index and the fat index, and
a nutritional ingredient instruction circuit configured to send an instruction to the generating apparatus to extract a quantity of the supplement material having the determined nutritional ingredients from a supplement storage container, and dispense the determined nutritional ingredients to the user to allow the user to achieve a desired body type,
wherein the processor is configured to
determine an effect that previously ingested nutritional ingredients that were received from the generating apparatus based on a previously measured muscle index and previously measured fat index that had been measured by the body composition measuring apparatus and stored in the processor had on the change in the body shape of the user, and
determine a supplemental nutritional ingredient which supplements the nutritional ingredients based on the effect of the previously ingested nutritional ingredients and on a divergence from the body shape of the user to the target body shape such that the increasing ingredient which increases muscle is included when a muscle index component of the divergence is above a second threshold.

2. An ingredient determining apparatus as defined in claim 1, wherein
based on a biometric index that identifies a risk of a predetermined lifestyle disease, the processor is configured to determine an improvement ingredient for the biometric index to be included in the nutritional ingredients.

3. An ingredient determining apparatus as defined in claim 2, wherein
the biometric index includes at least one of basal metabolism, visceral fat and bone mass of the user,
the improvement ingredient for the basal metabolism includes at least one of an ingredient which activates the basal metabolism and an ingredient which promotes blood circulation,
the improvement ingredient for the visceral fat includes at least one of an antioxidant ingredient, an ingredient which decomposes fat and an ingredient which promotes metabolism of lipid, and
the improvement ingredient for the bone mass includes at least one of an ingredient which forms bone and an ingredient which assists metabolism of bone.

4. An ingredient determining apparatus as defined in claim 1, wherein
the processor is configured to calculate the nutritional ingredients required for managing a body shape of the user based on the muscle index and the fat index.

5. An ingredient determining apparatus as defined in claim 1, further comprising
a memory configured to hold the nutritional ingredients required for managing a body shape of the user in association with each of predetermined body shape types, wherein
the processor is configured to:
select a body shape type to which the body shape of the user belongs from among predetermined body shape types based on the muscle index and the fat index; and
calculate the nutritional ingredients associated with the body shape type referring to the memory based on the body shape type selected.

6. An ingredient determining apparatus as defined in claim 1, wherein
the nutritional ingredients include an inhibitory ingredient which inhibits fat from accumulating and an activating ingredient which activates vitality of the user, and
as the fat index increases, the processor is configured to increase the inhibitory ingredient and decrease the activating ingredient.

7. An ingredient determining apparatus as defined in claim 1, wherein
the nutritional ingredients include a fitting ingredient which keeps muscle healthy and an increasing ingredient which increases muscle, and
as the muscle index increases, the processor is configured to increase the fitting ingredient and decrease the increasing ingredient.

8. An ingredient determining apparatus as defined in claim 1, wherein
the processor is configured to determine the supplemental nutritional ingredient such that an inhibitory ingredient which inhibits fat from accumulating is included when a fat index component of the divergence is below a first threshold.

9. An ingredient determining apparatus as defined in claim 1, wherein
the nutritional ingredients include carbohydrate, and
as a muscle index component of the divergence increases, the processor is configured to increase a supplemental amount of the carbohydrate.

10. An ingredient determining apparatus as defined in claim 1, wherein
the muscle index is muscle mass or a parameter that correlates with muscle mass of the user, and
the fat index is a fat rate of the user.

11. An ingredient determining apparatus as defined in claim 1, wherein
the processor is further configured to determine an adjustment ingredient which conditions a body as another nutritional ingredient based on an evaluation value of at least one of exhalation, physical activity and sleep of the user.

12. An ingredient determining method for determining nutritional ingredients in food provided for a user, comprising:
a step of receiving body shape data indicating a target body shape targeted by the user,
a step of obtaining a muscle index indicating a degree of muscle mass of the user and a fat index indicating a degree of fat mass of the user from a body composition measuring apparatus that is configured to measure impedance of at least one body part of the user from a voltage value detected by a voltage detecting circuit, and then calculate the muscle index and the fat index based on the measured impedance values,
a step of determining the nutritional ingredients based on the muscle index and the fat index, and
a step of instructing a generating apparatus to extract a quantity of the supplement material having the determined nutritional ingredients from a supplement storage container, and dispense the determined nutritional ingredients to the user to allow the user to achieve a desired body type,
wherein in the determining step, an effect that previously ingested nutritional ingredients that were received from the generating apparatus based on a previously measured muscle index and previously measured fat index that had been measured by the body composition measuring apparatus and stored in the processor had on the change in the body shape of the user is also determined, and
a supplemental nutritional ingredient which supplements the nutritional ingredients based on the effect of the previously ingested nutritional ingredients and on a divergence from the body shape of the user to the target body shape such that the increasing ingredient which increases muscle is included when a muscle index component of the divergence is above a second threshold is determined.

13. A non-transitory computer-readable recording medium including a program configured to cause a computer determining nutritional ingredients in food provided for a user to execute following steps:
a step of receiving body shape data indicating a target body shape targeted by the user,
a step of obtaining a muscle index indicating a degree of muscle mass of the user and a fat index indicating a degree of fat mass of the user from a body composition measuring apparatus that is configured to measure impedance of at least one body part of the user from a voltage value detected by a voltage detecting circuit, and then calculate the muscle index and the fat index based on the measured impedance values,
a step of determining the nutritional ingredients based on the muscle index and the fat index, and
a step of instructing a generating apparatus to extract a quantity of the supplement material having the determined nutritional ingredients from a supplement storage container, and dispense the determined nutritional ingredients to the user to allow the user to achieve a desired body type,
wherein in the determining step, an effect that previously ingested nutritional ingredients that were received from the generating apparatus based on a previously measured muscle index and previously measured fat index that had been measured by the body composition measuring apparatus and stored in the processor had on the change in the body shape of the user is also determined, and
a supplemental nutritional ingredient which supplements the nutritional ingredients based on the effect of the previously ingested nutritional ingredients and on a divergence from the body shape of the user to the target body shape such that the increasing ingredient which increases muscle is included when a muscle index component of the divergence is above a second threshold is determined.

* * * * *